United States Patent
Kim et al.

(10) Patent No.: US 11,168,081 B2
(45) Date of Patent: Nov. 9, 2021

(54) ALKALOID DERIVATIVE HAVING ANGIOGENESIS INHIBITORY EFFECT, AND PHARMACEUTICAL COMPOSITION CONTAINING SAME

(71) Applicant: SEOUL NATIONAL UNIVERSITY R&DB FOUNDATION, Seoul (KR)

(72) Inventors: Sanghee Kim, Seoul (KR); Sang Kook Lee, Seoul (KR); Jedo Oh, Seoul (KR); Feng Li, Seoul (KR); Shuai Yu, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 16/633,619

(22) PCT Filed: Jul. 20, 2018

(86) PCT No.: PCT/KR2018/008248
§ 371 (c)(1),
(2) Date: Jan. 24, 2020

(87) PCT Pub. No.: WO2019/022444
PCT Pub. Date: Jan. 31, 2019

(65) Prior Publication Data
US 2021/0087185 A1    Mar. 25, 2021

(30) Foreign Application Priority Data
Jul. 25, 2017  (KR) .................. 10-2017-0094430

(51) Int. Cl.
*C07D 417/14*   (2006.01)
*A61P 27/02*    (2006.01)
*C07D 417/06*   (2006.01)
*C07D 405/06*   (2006.01)
*C07D 413/06*   (2006.01)

(52) U.S. Cl.
CPC ............ *C07D 417/14* (2013.01); *A61P 27/02* (2018.01); *C07D 405/06* (2013.01); *C07D 413/06* (2013.01); *C07D 417/06* (2013.01)

(58) Field of Classification Search
CPC .. C07D 417/14; C07D 405/06; C07D 413/06; C07D 417/06; A61P 27/02
USPC ...................................... 514/233.8
See application file for complete search history.

(56) References Cited

FOREIGN PATENT DOCUMENTS

| KR | 10-0404580 B1 | 11/2003 |
| KR | 10-2011-0039842 A | 4/2011 |
| KR | 10-2012-0122705 A | 11/2012 |

OTHER PUBLICATIONS

Byung-Hak Kim et al., "Imidazole-based alkaloid derivative LCB54-0009 suppresses ocular angiogenesis and lymphangiogenesis in models of experimental retinopathy and corneal neovascularization", British Journal of Pharmacology, 2015, pp. 3875-3889, vol. 172.
Shuai Yu et al., "New Scaffold for Angiogenesis Inhibitors Discovered by Targeted Chemical Transformations of Wondonin Natural Products", ACS Medicinal Chemistry Letters, Sep. 12, 2017, pp. 1066-1071, vol. 8, No. 10.
Hyoung-Oh Jun et al., "Wondonin, a novel compound, inhibits hypoxia-induced angiogenesis through hypoxia-inducible factor 1 alpha", FEBS Letters, 2007, pp. 4977-4982, vol. 581.
International Search Report for PCT/KR2018/008248 dated Oct. 31, 2018. [PCT/ISA/210].

*Primary Examiner* — Kristin A Vajda
(74) *Attorney, Agent, or Firm* — Sughrue Mion, PLLC

(57) ABSTRACT

An alkaloid derivative having an activity of inhibiting angiogenesis and having structural stability is disclosed. A pharmaceutical composition containing the alkaloid derivative and its use are disclosed. The alkaloid derivative can be effectively used for treating or preventing diabetic retinopathy, cancer, duodenal ulcer, arthritis or obesity.

10 Claims, 5 Drawing Sheets

ALKALOID DERIVATIVE HAVING ANGIOGENESIS INHIBITORY EFFECT, AND PHARMACEUTICAL COMPOSITION CONTAINING SAME

CROSS REFERENCE TO RELATED APPLICATIONS

This application is a National Stage of International Application No. PCT/KR2018/008248 filed Jul. 20, 2018, claiming priority based on Korean Patent Application No. 10-2017-0094430 filed Jul. 25, 2017, and the disclosure of which is incorporated herein in its entirety.

TECHNICAL FIELD

The present invention relates to an alkaloid derivative having vascular tube formation inhibition effect and a pharmaceutical composition comprising the same. More particularly, the present invention relates to an alkaloid derivative which inhibits angiogenesis by suppressing vascular endothelial growth factor (VEGF) signaling pathway and has structural stability, and a pharmaceutical composition comprising the same as an active ingredient.

BACKGROUND ART

VEGF is a signaling protein which stimulates angiogenesis, and an important in vivo signaling protein which is expressed under hypoxia in blood vessels and forms new blood vessels. Particularly, VEGF is a protein which is highly related to diseases causing aberrant angiogenesis such as diabetic retinopathy, cancer, duodenal ulcer, arthritis, and obesity.

Wondonin of the following formula (1) is a structurally unique marine alkaloid that was identified from an association of the sponges *Poecillatra wondoensis* and *Jaspis* sp. In contrast to conventional VEGF inhibitors, wondonin does not inhibit human umbilical vascular endothelial cell (HU-VEC), and thus effectively inhibits VEGF without cytotoxicity to inhibit angiogenesis [Korean Patent Application Publication No. 10-2012-0122705].

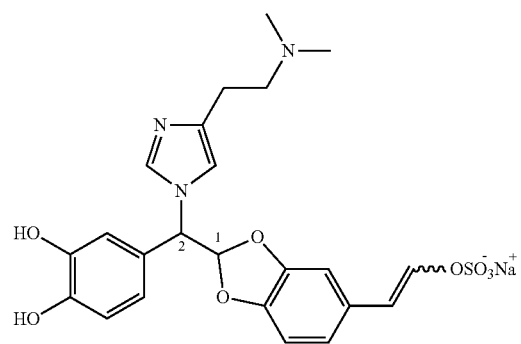

(1)

However, wondonin has a structural instability derived from the benzodioxole moiety, and thus has problems that the stability is lowered during the preparation and storage and it is difficult to achieve in vivo activity.

DISCLOSURE

Technical Problem

It is an object of the present invention to provide an alkaloid derivative of the following formula (I) which inhibits angiogenesis by inhibiting VEGF signaling pathway and has structural stability, or pharmaceutically acceptable salt thereof.

It is another object of the present invention to provide a pharmaceutical composition for inhibiting vascular tube formation containing an alkaloid derivative of the following formula (I) or pharmaceutically acceptable salt thereof.

Technical Solution

One embodiment of the present invention relates to an alkaloid derivative of the following formula (I) or pharmaceutically acceptable salt thereof:

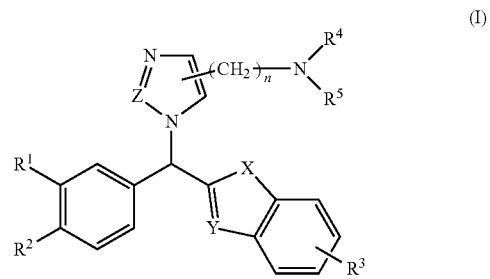

(I)

wherein,
X is oxygen or sulfur atom,
Y is nitrogen or carbon atom,
Z is nitrogen or carbon atom,
$R^1$ and $R^2$ are each independently hydrogen, hydroxyl, or $C_1$-$C_6$ alkoxy,
$R^3$ is $C_1$-$C_6$ alkyl,
$R^4$ and $R^5$ are each independently hydrogen, $C_1$-$C_6$ alkyl, or $C_3$-$C_{10}$ cycloalkyl, or
$R^4$ and $R^5$ form a 5- to 7-membered heterocycle in combination with nitrogen adjacent thereto, and
n is an integer of 0 to 6.

The term "$C_1$-$C_6$ alkoxy" as used herein means a straight or branched alkoxy group having 1 to 6 carbon atoms, which includes methoxy, ethoxy, n-propanoxy, etc., but is not limited thereto.

The term "$C_1$-$C_6$ alkyl" as used herein means a straight or branched monovalent hydrocarbon having 1 to 6 carbon atoms, which includes methyl, ethyl, n-propyl, propyl, n-butyl, i-butyl, t-butyl, n-pentyl, n-hexyl, etc., but is not limited thereto.

The term "$C_3$-$C_{10}$ cycloalkyl" as used herein means a simple or fused cyclic hydrocarbon having 3 to 10 carbon atoms, which includes cyclopropyl, cyclobutyl, cyclopentyl, cyclohexyl, etc., but is not limited thereto.

The term "5- to 7-membered heterocycle" as used herein means a pentagonal to heptagonal ring having 1 to 3 hetero atoms selected from the group consisting of oxygen, sulfur and nitrogen, which includes piperidine, morpholine or pyrimidine, etc., but is not limited thereto.

In one embodiment of the present invention, the alkaloid derivative is a compound,
wherein,
X is oxygen atom,
Y is carbon atom, and
Z is nitrogen or carbon atom.

In one embodiment of the present invention, the alkaloid derivative is a compound, wherein,
X is sulfur atom,
Y is nitrogen atom, and
Z is nitrogen or carbon atom.

In one embodiment of the present invention, the alkaloid derivative is a compound,
wherein,
X is sulfur atom,
Y is nitrogen atom,
Z is nitrogen or carbon atom,
$R^1$ and $R^2$ are each independently hydroxyl or $C_1$-$C_6$ alkoxy,
$R^3$ is $C_1$-$C_6$ alkyl,
$R^4$ and $R^5$ are each independently hydrogen, $C_1$-$C_6$ alkyl, or $C_3$-$C_{10}$ cycloalkyl, or
$R^4$ and $R^5$ form a 5- to 7-membered heterocycle in combination with nitrogen adjacent thereto, and
n is an integer of 0 to 6.

In one embodiment of the present invention, the alkaloid derivative is a compound,
wherein,
X is sulfur atom,
Y is nitrogen atom,
Z is nitrogen atom,
$R^1$ and $R^2$ are each independently hydroxyl or $C_1$-$C_6$ alkoxy,
$R^3$ is $C_1$-$C_6$ alkyl,
$R^4$ and $R^5$ are each independently hydrogen, $C_1$-$C_6$ alkyl, or $C_3$-$C_{10}$ cycloalkyl, or
$R^4$ and $R^5$ form a 5- to 7-membered heterocycle in combination with nitrogen adjacent thereto, and
n is an integer of 0 to 6.

The pharmaceutically acceptable salt of the present invention may include salts of nontoxic inorganic acid and organic acid such as hydrochloride, sulfate, nitrate, phosphate, acetate, adipate, aspartate, benzoate, benzenesulfonate, citrate, camphorate, camphosulfonate, diphosphate, ethanesulfonate, fumarate, glutamate, maleate, lactate, methanesulfonate, succinate, tartrate, picrate, tosylate, etc.

The representative compounds according to the present invention are selected from the following group.

4-((4-(2-(dimethylamino)ethyl)-1H-1,2,3-triazol-1-yl)(6-ethylbenzo[d]thiazol-2-yl)methyl)benzene-1,2-diol (I-1);

2-(1-((3,4-dimethoxyphenyl)(6-ethylbenzo[d]thiazol-2-yl)methyl)-1H-1,2,3-triazol-4-yl)-N,N-dimethylethan-1-amine (I-2);

N-(2-(1-((3,4-dimethoxyphenyl)(6-ethylbenzo[d]thiazol-2-yl)methyl)-1H-1,2,3-triazol-4-yl)ethyl)propan-1-amine (I-3);

N-(2-(1-((3,4-dimethoxyphenyl)(6-ethylbenzo[d]thiazol-2-yl)methyl)-1H-1,2,3-triazol-4-yl)ethyl)cyclopentanamine (I-4);

2-((3,4-dimethoxyphenyl)(4-(2-(pyrrolidin-1-yl)ethyl)-1H-1,2,3-triazol-1-yl)methyl)-6-ethylbenzo[d]thiazole (I-5);

4-(2-(1-((3,4-dimethoxyphenyl)(6-ethylbenzo[d]thiazol-2-yl)methyl)-1H-1,2,3-triazol-4-yl)ethyl)morpholine (I-6);

2-((3,4-dimethoxyphenyl)(4-(2-(piperidin-1-yl)ethyl)-1H-1,2,3-triazol-1-yl)methyl)-6-ethylbenzo[d]thiazole (I-7);

4-((4-(2-(dimethylamino)ethyl)-1H-1,2,3-triazol-1-yl)(6-ethylbenzofuran-2-yl)methyl)benzene-1,2-diol (I-8);

4-((4-(2-(dimethylamino)ethyl)-1H-1,2,3-triazol-1-yl)(6-ethylbenzo[d]oxazol-2-yl)methyl)benzene-1,2-diol (I-9);

2-(1-((3,4-dimethoxyphenyl)(6-ethylbenzo[d]thiazol-2-yl)methyl)-1H-imidazol-4-yl)-N,N-dimethylethan-1-amine (I-10);

N-(2-(1-((3,4-dimethoxyphenyl)(6-ethylbenzo[d]thiazol-2-yl)methyl)-1H-imidazol-4-yl)ethyl)-N-propylpropan-1-amine (I-11);

2-((3,4-dimethoxyphenyl)(4-(2-(piperidin-1-yl)ethyl)-1H-imidazol-1-yl)methyl)-6-ethylbenzo[d]thiazole (I-12);

N-(2-(1-((3,4-dimethoxyphenyl)(6-ethylbenzo[d]thiazol-2-yl)methyl)-1H-imidazol-4-yl)ethyl)cyclopentanamine (I-13);

2-((3,4-dimethoxyphenyl)(4-(2-(pyrrolidin-1-yl)ethyl)-1H-imidazol-1-yl)methyl)-6-ethylbenzo[d]thiazole (I-14);

2-((3,4-dimethoxyphenyl)(4-(piperidin-1-ylmethyl)-1H-1,2,3-triazol-1-yl)methyl)-6-ethylbenzo[d]thiazole (I-15); and 2-((3,4-dimethoxyphenyl)(4-(3-(piperidin-1-yl)propyl)-1H-1,2,3-triazol-1-yl)methyl)-6-ethylbenzo[d]thiazole (I-16).

The processes for preparing the alkaloid derivative of formula (I) of the present invention are shown in the following reaction schemes 1 to 3. The processes depicted in the following reaction schemes represent merely typical examples, and various changes may be made to reagents, reaction conditions, etc. without limitation.

[Reaction Scheme 1]

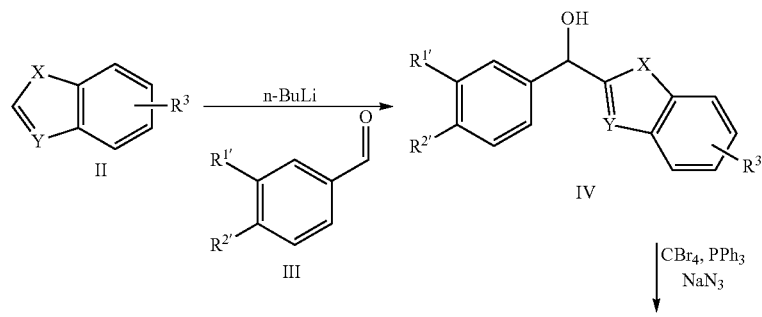

-continued

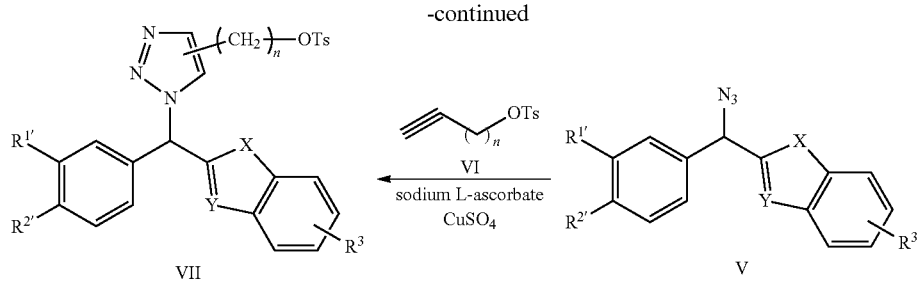

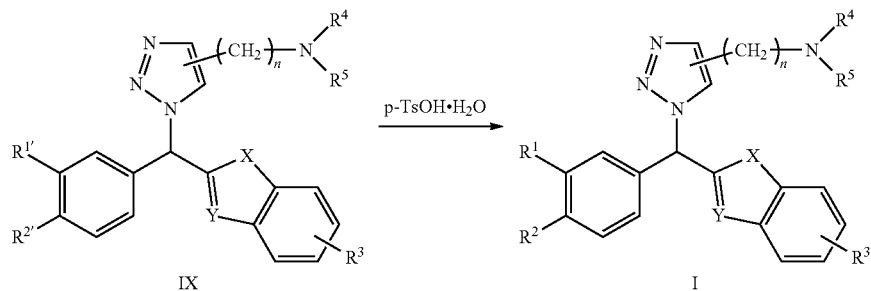

As shown in the reaction scheme 1, the alkaloid derivative of formula (I) wherein Z is nitrogen atom can be prepared by reacting a compound of formula (II) with a compound of formula (III) in the presence of a base such as n-butyl lithium to obtain a compound of formula (IV), subjecting the hydroxyl group of the compound of formula (IV) to a substitution reaction with an azide such as $NaN_3$ and $KN_3$ to obtain a compound of formula (V), subjecting the compound of formula (V) to an azide-alkyne combination reaction with a compound of formula (VI) to obtain a compound of formula (VII), reacting the compound of formula (VII) with a compound of formula (VIII) to obtain a compound of (IX), and then selectively deprotecting the compound of formula (IX) if $R^{1'}$ and/or $R^{2'}$ are protected hydroxyl.

The substitution reaction of the hydroxyl group with the azide can be carried out in the presence of triphenylphosphine ($PPh_3$) and tetrabromomethane ($CBr_4$).

Further, the azide-alkyne combination reaction can be carried out using a copper salt such as $CuSO_4$ as a catalyst in the presence of a reductant such as sodium L-ascorbate.

The deprotection can be carried out with a catalyst which is appropriately selected depending on the type of the protecting group. For example, if the protecting group is MOM, p-TsOH can be used.

[Reaction Scheme 2]

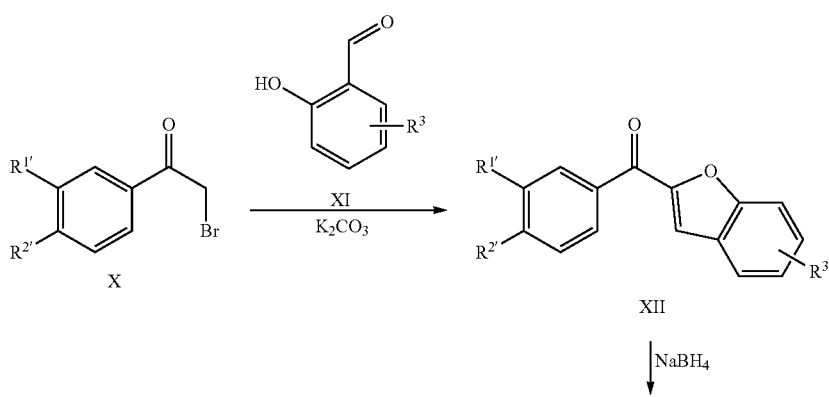

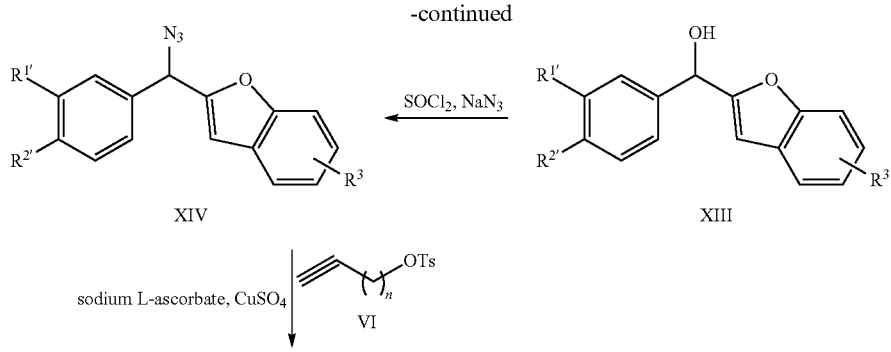

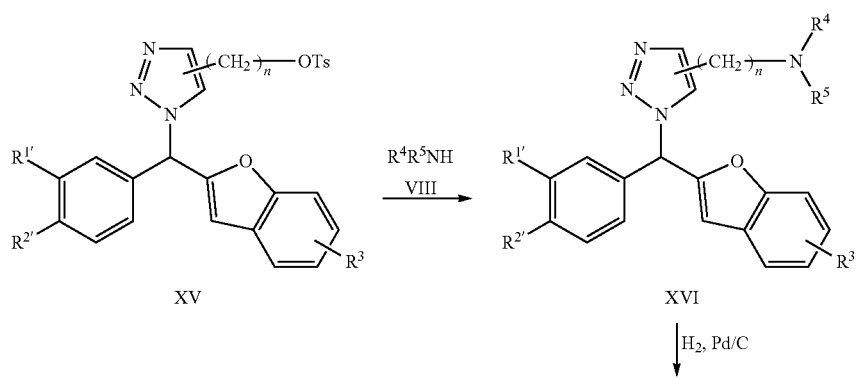

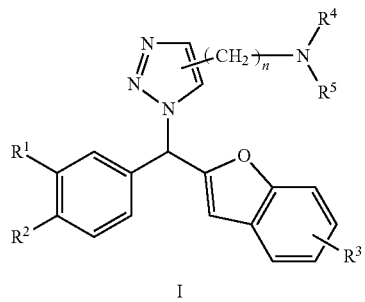

As shown in the reaction scheme 2, the alkaloid derivative of formula (I) wherein X is oxygen atom, Y is carbon atom, and Z is nitrogen atom can be prepared by subjecting a compound of formula (X) to a Rap-Stoermer condensation reaction with a compound of formula (XI) in the presence of a base such as $K_2CO_3$ to obtain a compound of formula (XII), reducing the ketone group of the compound of formula (XII) using $NaBH_4$ and the like to obtain a compound of formula (XIII), subjecting the hydroxyl group of the compound of formula (XIII) to a substitution reaction with an azide such as $NaN_3$ and $KN_3$ to obtain a compound of formula (XIV), subjecting the compound of formula (XIV) to an azide-alkyne combination reaction with a compound of formula (VI) to obtain a compound of formula (XV), react-ing the compound of formula (XV) with a compound of formula (VIII) to obtain a compound of formula (XVI), and then selectively deprotecting the compound of formula (XVI) if $R^{1'}$ and/or $R^{2'}$ are protected hydroxyl.

The substitution reaction of the hydroxyl group with the azide can be carried out in the presence of $SOCl_2$.

Further, the azide-alkyne combination reaction can be carried out using a copper salt such as $CuSO_4$ as a catalyst in the presence of a reductant such as sodium L-ascorbate.

The deprotection can be carried out with a catalyst which is appropriately selected depending on the type of the protecting group. For example, if the protecting group is Bn, the deprotection can be carried out by hydrogenation in the presence of Pd/C.

[Reaction Scheme 3]

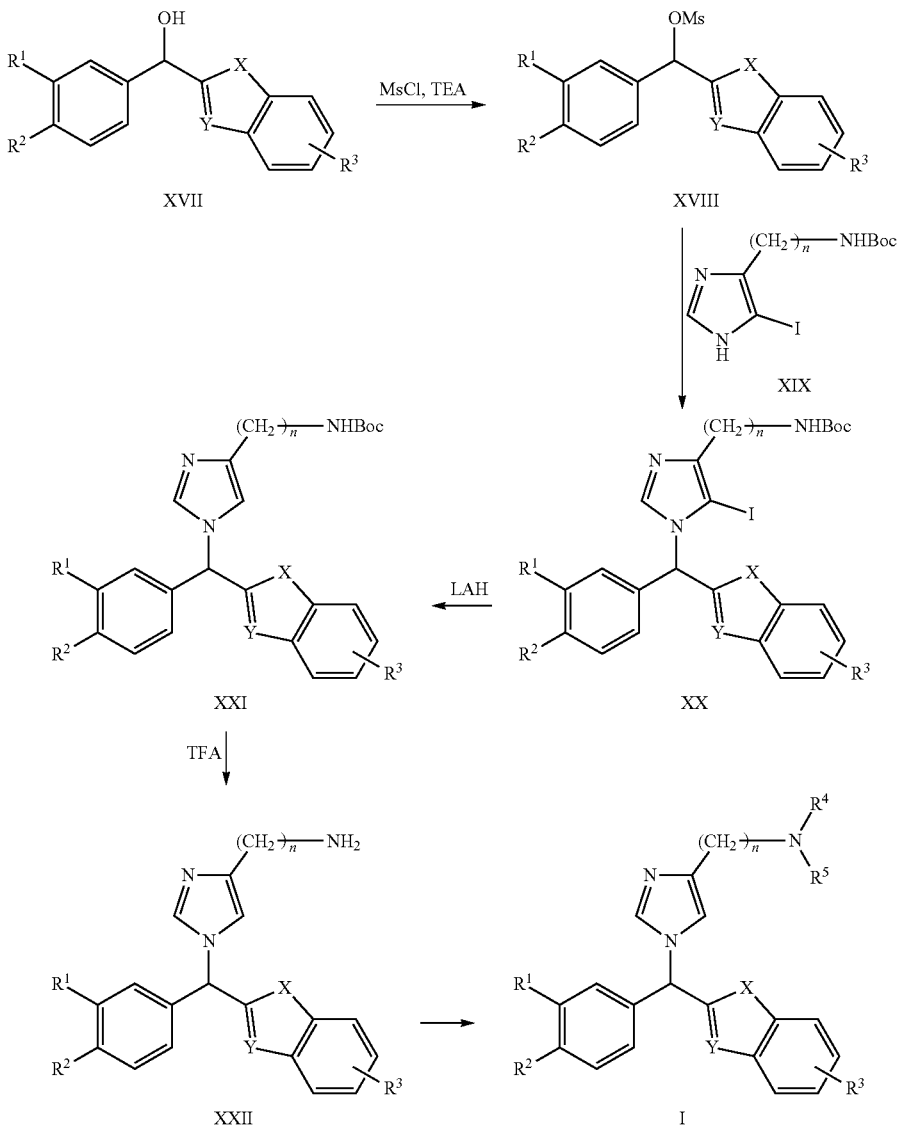

As shown in the reaction scheme 3, the alkaloid derivative of formula (I) wherein Z is carbon atom can be prepared by reacting a compound of formula (XVII) with methanesulfonyl chloride in the presence of a base such as triethylamine (TEA) to obtain a compound of formula (XVIII), reacting the compound of formula (XVIII) with a compound of formula (XIX) to obtain a compound of formula (XX), reducing the compound of formula (XX) using lithium aluminum hydride (LAH) and the like to obtain a compound of formula (XXI), deprotecting the amine group of the compound of formula (XXI) using trifluoroacetic acid (TFA) and the like to obtain a compound of formula (XXII), and then subjecting the amine group of the compound of formula (XXII) to alkylation.

The alkylation of the amine group can be carried out by reductive amination of an aldehyde or ketone, or reaction with an alkyl halide.

The compound of formula (I) according to the present invention or pharmaceutically acceptable salt thereof exhibits its excellent angiogenic inhibition activity by inhibiting vascular tube formation induced by vascular endothelial growth factor (VEGF) without cytotoxicity to human umbilical vascular endothelial cell (HUVEC) (see Experimental Examples 1 and 2).

Also, the compound of formula (I) according to the present invention or pharmaceutically acceptable salt thereof has structural stability, and thus exhibits high plasma stability (see Experimental Example 3).

Further, the compound of formula (I) according to the present invention or pharmaceutically acceptable salt thereof exhibits angiogenic inhibition potency in a diabetic retinopathy animal model experiment (see Experimental Example 4).

Accordingly, the present invention relates to a pharmaceutical composition for inhibiting signaling pathway which mediates vascular tube formation, comprising the compound of formula (I) or pharmaceutically acceptable salt thereof together with a pharmaceutically acceptable carrier. Specifically, the present invention relates to a pharmaceutical composition for treating or preventing diabetic retinopathy, cancer, duodenal ulcer, arthritis or obesity, particularly diabetic retinopathy.

The pharmaceutical composition according to the present invention can be administered orally (e.g., ingestion or inhalation); or parenterally (e.g., injection, deposition, implantation or suppositories). The injection can be, for example, intravenous, subcutaneous, intramuscular or intraperitoneal. Depending on the route of administration, the pharmaceutical composition according to the present invention may be formulated as tablets, capsules, granules, fine subtilae, powders, sublingual tablets, suppositories, ointments, injection solutions, emulsions, suspensions, syrups, aerosols, etc. The above various forms of the pharmaceutical composition according to the present invention can be prepared in a manner well known in the art using a pharmaceutically acceptable carrier(s) which is(are) usually used for each form. Examples of the pharmaceutically acceptable carriers include excipient, binder, disintegrating agent, lubricant, preservative, antioxidant, isotonic agent, buffer, coating agent, sweetening agent, dissolvent, base, dispersing agent, wetting agent, suspending agent, stabilizer, colorant, etc.

The pharmaceutical composition according to the present invention comprises 0.01 to 95 wt % of the compound of the present invention or pharmaceutically acceptable salt thereof depending on the form thereof.

The specific dosage of the present pharmaceutical composition can be varied with species of mammals including a human-being, body weight, gender, severity of disease, judgment of doctor, etc. It is preferable that 0.01 to 50 mg of the active ingredient is administered per kg of body weight a day for oral use, while 0.01 to 10 mg of the active ingredient is administered per kg of body weight a day for parenteral use. The total daily dosage can be administered once or over several times depending on the severity of disease, judgment of doctor, etc.

Advantageous Effects

The compound of the present invention does not inhibit human umbilical vascular endothelial cell (HUVEC), and thus exhibits excellent angiogenesis inhibition activity by inhibiting vascular endothelial growth factor (VEGF)-induced vascular tube formation without cytotoxicity. Also, the compound of the present invention has structural stability and thus has excellent stability during the preparation and storage and exhibits high plasma stability. Therefore, the compound of the present invention can be effectively used for a pharmaceutical composition for treating or preventing diabetic retinopathy, cancer, duodenal ulcer, arthritis or obesity.

BEST MODE

Figure 1A:
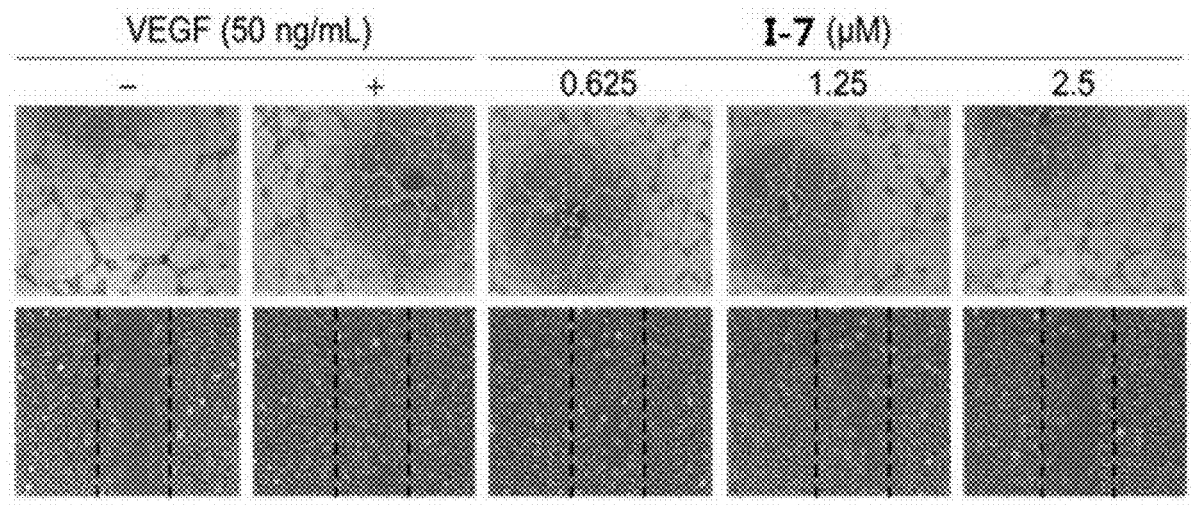
FIG. 1(A) is a photograph of scratch wound migration assay of the compound (I-7) of Example 7 (upper panel), and of endothelial cell tubular structure formation assay of the compound (I-7) of Example 7 (lower panel).

The present invention will be described below in more detail by following examples. It will be obvious to those skilled in the art that these examples are merely described for illustration of the present invention and the scope of the present invention is not limited thereto.

Preparation Example 1: Preparation of Compound of Formula (II)

Preparation Example 1-1: 6-ethylbenzo[d]thiazole (II-1)

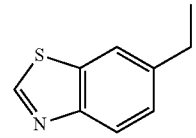

To a stirred solution of 2-amino-6-ethylbenzo[d]thiazole (1.1 g, 6.17 mmol) in 20 mL of DMF was added tert-butyl nitrite (1.1 mL, 9.25 mmol), and the mixture was stirred at 50° C. for 3 hours. The reaction product was diluted with $H_2O$, and extracted with EtOAc. The organic layer was dried over $MgSO_4$ and concentrated in vacuo. The crude product was separated by silica gel column chromatography (hexane/EtOAc, 30:1) to give the title compound (II-1) (604 mg, 60%) as a dark red oil.

$^1$H NMR (300 MHz, $CDCl_3$) δ 8.89 (s, 1H), 8.02 (d, J=8.2 Hz, 1H), 7.75 (d, J=0.9 Hz, 1H), 7.34 (dd, J=1.7 Hz, 8.3 Hz, 1H), 2.75 (q, J=7.5 Hz, 2H), 1.29 (t, J=7.5 Hz, 3H);

$^{13}$C NMR (75 MHz, $CDCl_3$) δ 152.9, 142.0, 133.8, 126.7, 123.1, 120.2, 28.8, 15.8;

IR ($CHCl_3$) $v_{max}$ 2964, 1469, 1407, 1291, 891, 824 ($cm^{-1}$);

HRMS (FAB): calcd. for $C_9H_{10}NS[M+H]^+$ 164.0534, found 164.0540.

Preparation Example 1-2: 6-ethylbenzo[d]oxazole (II-2)

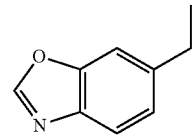

To a stirred solution of 5-ethyl-2-nitrophenol (879 mg, 5.26 mmol) in 15 mL of benzene were added indium (2.4 g, 21.1 mmol), AcOH (3 mL, 52.6 mmol) and trimethyl orthoformate (2.3 mL, 21.1 mmol), and the mixture was refluxed for 1 hour. After cooling to room temperature, the reaction product was diluted with $H_2O$, and extracted with $CH_2Cl_2$. The organic layer was dried over $MgSO_4$ and concentrated in vacuo. The crude product was separated by silica gel column chromatography (hexane/EtOAc, 10:1) to give the title compound (II-2) (587 mg, 76%) as a yellow oil.

$^1$H NMR (300 MHz, CDCl$_3$) δ 8.01 (s, 1H), 7.65 (d, J=8.2 Hz, 1H), 7.37 (s, 1H), 7.18 (dd, J=1.2 Hz, 8.2 Hz, 1H), 2.75 (q, J=7.6 Hz, 2H), 1.26 (t, J=7.6 Hz, 3H);

$^{13}$C NMR (75 MHz, CDCl$_3$) δ 152.0, 150.2, 142.5, 137.9, 124.7, 119.9, 109.7, 29.0, 15.8;

IR (CHCl$_3$) ν$_{max}$ 3290 (br), 2968, 1670, 1603, 1530 (cm$^{-1}$);

HRMS (FAB): calcd. for C$_9$H$_{10}$NO [M+H]$^+$ 148.0762, found 148.0760.

Preparation Example 2: Preparation of Compound of Formula (IV)

Preparation Example 2-1: (3,4-dimethoxyphenyl)(6-ethylbenzo[d]thiazol-2-yl)methanol (IV-1

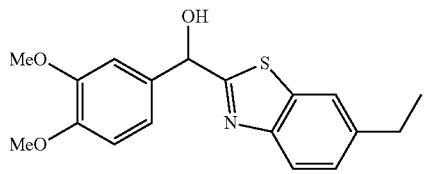 [SMILES: CCc1ccc2nc(C(O)c3ccc(OC)c(OC)c3)sc2c1]

To a stirred solution of the compound (II-1) obtained in Preparation Example 1-1 (475 mg, 2.91 mmol) in 8 mL of dry THF was added n-BuLi (2.0 mL, 3.2 mmol, 1.6 M solution in hexane), and the mixture was stirred at 78° C. for 1 hour. To the reaction mixture was added 3,4-dimethoxybenzaldehyde (483 mg, 2.91 mmol), and the mixture was stirred at room temperature for 12 hours. The reaction mixture was diluted with H$_2$O, and extracted with EtOAc. The organic layer was dried over MgSO$_4$ and concentrated in vacuo. The crude product was separated by silica gel column chromatography (hexane/EtOAc, 2:1) to give the title compound (IV-1) (355 mg, 37%) as a yellow oil.

$^1$H NMR (400 MHz, CDCl$_3$) δ 7.88 (d, J=8.4 Hz, 1H), 7.62 (s, 1H), 7.29 (dd, J=1.6 Hz, 8.2 Hz, 1H), 7.06-7.02 (m, 2H), 6.84 (d, J=8.1 Hz, 1H), 6.06 (s, 1H), 2.96 (s, 3H), 2.94 (s, 3H), 2.74 (q, J=7.5 Hz, 2H), 1.26 (t, J=7.5 Hz, 3H);

$^{13}$C NMR (75 MHz, CDCl$_3$) δ 174.0, 150.3, 149.2, 141.8, 135.3, 133.3, 126.7, 122.5, 120.3, 119.2, 110.9, 109.4, 74.1, 55.8, 28.9, 15.8;

IR (CHCl$_3$) ν$_{max}$ 3222 (br), 2962, 1594, 1507, 1257, 1151, 1072, 985, 824 (cm$^{-1}$);

HRMS (FAB): calcd. for C$_{18}$H$_{20}$NO$_3$S [M+H]$^+$ 330.1164, found 330.1161.

Preparation Example 2-2: (3,4-bis(methoxymethoxy)phenyl)(6-ethylbenzo[d]thiazol-2-yl)methanol (IV-2

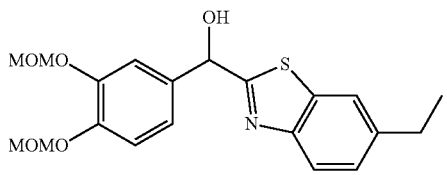

The title compound was synthesized in the same manner as in Preparation Example 2-1, except for using the compound (II-1) obtained in Preparation Example 1-1 (320 mg, 1.96 mmol) and 3,4-bis(methoxymethoxy)benzaldehyde (487 mg, 2.2 mmol). The crude product was separated by silica gel column chromatography (hexane/EtOAc, 2:1) to give the title compound (IV-2) (236 mg, 31%) as a yellow oil.

$^1$H NMR (300 MHz, CDCl$_3$) δ 7.82 (d, J=8.2 Hz, 1H), 7.61 (d, J=1.1 Hz, 1H), 7.31 (d, J=1.6 Hz, 1H), 7.26-7.22 (m, 1H), 7.08-7.06 (m, 2H), 5.98 (s, 1H), 5.17 (s, 4H), 3.45 (s, 6H), 2.72 (q, J=7.6 Hz, 2H), 1.24 (t, J=7.6 Hz, 3H);

$^{13}$C NMR (75 MHz, CDCl$_3$) δ 174.3, 150.8, 147.3, 147.2, 141.5, 135.4, 135.3, 126.5, 122.5, 120.9, 120.2, 116.7, 115.3, 95.3, 73.8, 56.1, 28.8, 15.7;

IR (CHCl$_3$) ν$_{max}$ 3209 (br), 2963, 1506, 1256, 1151, 1071, 984, 749 (cm$^{-1}$);

HRMS (FAB): calcd. for C$_{20}$H$_{24}$NO$_5$S [M+H]$^+$ 390.1375, found 390.1375.

Preparation Example 2-3: (3,4-bis(methoxymethoxy)phenyl)(6-ethylbenzo[d]oxazol-2-yl)methanol (IV-3

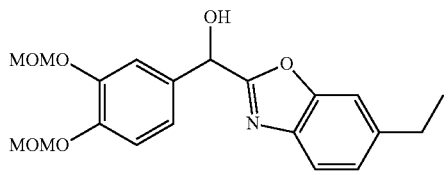

The title compound was synthesized in the same manner as in Preparation Example 2-1, except for using the compound (II-2) obtained in Preparation Example 1-2 (555 mg, 3.77 mmol) and 3,4-bis(methoxymethoxy)benzaldehyde (937 mg, 4.15 mmol). The crude product was separated by silica gel column chromatography (hexane/EtOAc, 2:1) to give the title compound (IV-3) (464 mg, 33%) as a yellow oil.

$^1$H NMR (300 MHz, CDCl$_3$) δ 7.57 (d, J=8.4 Hz, 1H), 7.33 (d, J=2.1 Hz, 1H), 7.28 (s, 1H), 7.16-7.11 (m, 1H), 7.11 (d, J=4.5 Hz, 1H), 7.06 (dd, J=1.9 Hz, 8.2 Hz, 1H), 6.93 (dd, J=2.1 Hz, 8.1 Hz, 1H), 5.21 (s, 2H), 5.20 (s, 2H), 3.49 (s, 3H), 3.47 (s, 3H), 2.73 (q, J=7.5 Hz, 2H), 1.24 (t, J=7.5 Hz, 3H);

$^{13}$C NMR (75 MHz, CDCl$_3$) δ 147.3, 146.6, 142.3, 138.1, 135.4, 133.1, 124.7, 121.1, 120.9, 119.4, 116.8, 115.6, 115.4, 109.7, 95.4, 70.1, 65.0, 56.2, 29.0, 15.9;

IR (CHCl$_3$) ν$_{max}$ 3386 (br), 2902, 1508, 1256, 1150, 1070, 981, 920, 821 (cm$^{-1}$);

HRMS (FAB): calcd. for C$_{20}$H$_{24}$NO$_6$ [M+H]$^+$ 374.1604, found 374.1597.

Preparation Example 3: Preparation of Compound of Formula (VII)

Preparation Example 3-1: 2-(1-((3,4-dimethoxyphenyl)(6-ethylbenzo[d]thiazol-2-yl)methyl)-1H-1,2,3-triazol-4-yl)ethyl 4-methylbenzenesulfonate (VII-1

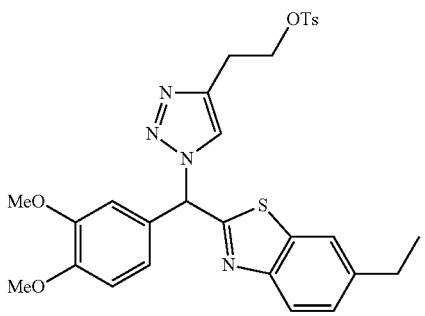 [SMILES: CCc1ccc2nc(C(c3ccc(OC)c(OC)c3)n3cc(CCOS(=O)(=O)c4ccc(C)cc4)nn3)sc2c1]

To a stirred solution of the compound (IV-1) obtained in Preparation Example 2-1 (331 mg, 1.0 mmol) in 8 mL of dry $CH_2Cl_2$ were added $PPh_3$ (633 mg, 2.41 mmol) and $CBr_4$ (800 mg, 2.41 mmol), and the mixture was stirred at room temperature for 20 minutes. To the reaction mixture was added $NaN_3$ (187 mg, 1.26 mmol), and the mixture was stirred at room temperature for 12 hours. The suspension was filtered over a cellite pad, and the filtrate was concentrated in vacuo. The crude azide was used for the following reaction without additional purification.

To a solution of the obtained azide (197 mg, 0.49 mmol) in 12 mL of t-BuOH/$H_2O$ (1/1 v/v) were added 3-butynyl p-toluenesulfonate (127 mg, 0.57 mmol), sodium L-ascorbate (48 mg, 0.24 mmol) and $CuSO_4 \cdot 5H_2O$ (12.6 mg, 0.049 mmol), and the mixture was heated at 60° C. for 2 hours. The suspension was diluted with $H_2O$, and extracted with EtOAc. The organic layer was dried over $MgSO_4$ and concentrated in vacuo. The crude product was separated by silica gel column chromatography (hexane/EtOAc, 1:1) to give the title compound (VII-1) (319 mg, 55%) as a yellow gum.

$^1$H NMR (300 MHz, $CDCl_3$) δ 7.96 (d, J=8.4 Hz, 1H), 7.70-7.63 (m, 7H), 7.34 (dd, J=1.4 Hz, 8.4 Hz, 1H), 6.78 (d, J=8.6 Hz, 1H), 6.52 (d, J=2.3 Hz, 1H), 6.37 (dd, J=2.3 Hz, 8.6 Hz, 1H), 4.24 (t, J=6.5 Hz, 2H), 3.85 (s, 3H), 3.62 (s, 3H), 3.06 (t, J=6.5 Hz, 2H), 2.74 (q, J=7.5 Hz, 2H), 2.33 (s, 3H), 1.23 (t, J=7.5 Hz, 3H);

$^{13}$C NMR (75 MHz, $CDCl_3$) δ 165.6, 151.1, 149.8, 149.3, 144.8, 142.7, 142.6, 135.5, 132.5, 129.8, 128.3, 127.8, 127.1, 123.3, 122.3, 120.7, 120.1, 111.1, 111.0, 68.7, 65.6, 56.0, 55.9, 28.9, 25.9, 21.6, 15.8;

IR ($CHCl_3$) $v_{max}$ 2964, 1598, 1516, 1357, 1262, 1175, 1025, 905, 815, 757 (cm$^{-1}$);

HRMS (FAB): calcd. for $C_{29}H_{31}N_4O_5S_2$ [M+H]$^+$ 579.1736, found 579.1734.

Preparation Example 3-2: 2-(1-((3,4-bis(methoxymethoxy)phenyl)(6-ethylbenzo[d]thiazol-2-yl)methyl)-1H-1,2,3-triazol-4-yl)ethyl 4-methylbenzenesulfonate (VII-2

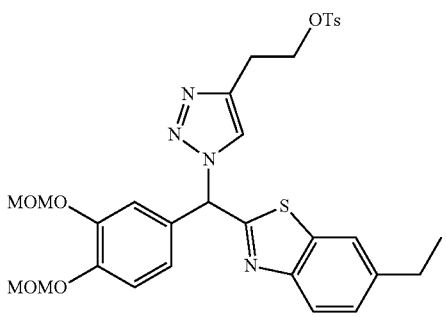

The title compound was synthesized in the same manner as in Preparation Example 3-1, except for using the compound (IV-2) obtained in Preparation Example 2-2 (210 mg, 0.54 mmol). The crude product was separated by silica gel column chromatography (hexane/EtOAc, 1:1) to give the title compound (VII-2) (196 mg, 57%) as a yellow oil.

$^1$H NMR (300 MHz, $CDCl_3$) δ 7.92 (d, J=8.4 Hz, 1H), 7.68-7.65 (m, 4H), 7.32 (dd, J=1.6 Hz, 8.5 Hz, 1H), 7.23-7.19 (m, 5H), 7.14 (d, J=8.7 Hz, 1H), 6.96 (dd, J=2.1 Hz, 8.7 Hz, 1H), 5.21 (s, 2H), 5.16 (s, 2H), 4.26 (t, J=6.4 Hz, 2H), 3.47 (s, 3H), 3.45 (s, 3H), 3.08 (t, J=6.4 Hz, 2H), 2.75 (q, J=7.6 Hz, 2H), 2.37 (s, 3H), 1.23 (t, J=7.6 Hz, 3H);

$^{13}$C NMR (75 MHz, $CDCl_3$) δ 165.4, 151.1, 148.2, 147.4, 144.8, 142.5, 135.5, 132.6, 129.7, 127.8, 127.1, 123.3, 122.2, 120.1, 116.9, 116.5, 95.5, 95.1, 68.7, 65.5, 56.3, 56.2, 28.9, 25.8, 21.5, 15.7;

IR ($CHCl_3$) $v_{max}$ 2962, 1598, 1510, 1357, 1257, 1174, 1074, 980, 752 (cm$^{-1}$);

HRMS (FAB): calcd. for $C_{31}H_{35}N_4O_7S_2$ [M+H]$^+$ 639.1947, found 639.1947.

Preparation Example 3-3: 2-(1-((3,4-bis(methoxymethoxy)phenyl)(6-ethylbenzo[d]oxazol-2-yl)methyl)-1H-1,2,3-triazol-4-yl)ethyl 4-methylbenzenesulfonate (VII-3

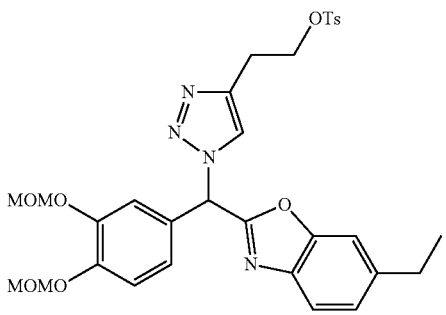

The title compound was synthesized in the same manner as in Preparation Example 3-1, except for using the compound (IV-3) obtained in Preparation Example 2-3 (297 mg, 0.79 mmol). The crude product was separated by silica gel column chromatography (hexane/EtOAc, 1.5:1) to give the title compound (VII-3) (260 mg, 53%) as a yellow oil.

¹H NMR (400 MHz, CDCl₃) δ 7.71 (s, 1H), 7.69 (d, J=5.7 Hz, 2H), 7.63 (d, J=8.2 Hz, 1H), 7.34 (s, 1H), 7.21-7.14 (m, 6H), 6.96 (dd, J=2.1 Hz, 8.4 Hz, 1H), 5.21 (s, 2H), 5.17 (d, J=1.9 Hz, 2H), 4.26 (t, J=6.8 Hz, 2H), 3.46 (s, 3H), 3.45 (s, 3H), 3.08 (t, J=6.8 Hz, 2H), 2.75 (q, J=7.6 Hz, 2H), 2.38 (s, 3H), 1.25 (t, J=7.6 Hz, 3H);

¹³C NMR (75 MHz, CDCl₃) δ 160.2, 151.1, 148.3, 147.5, 144.8, 143.1, 142.8, 138.4, 129.8, 127.9, 125.1, 122.0, 120.1, 116.7, 109.8, 95.6, 94.8, 68.6, 61.8, 56.3, 29.1, 25.9, 21.6, 15.9;

IR (CHCl₃) ν$_{max}$ 2964, 1512, 1360, 1260, 1175, 1077, 987 (cm⁻¹);

HRMS (FAB): calcd. for C₃₁H₃₅N₄O₈S [M+H]⁺ 623.2176, found 623.2183.

Preparation Example 4: Preparation of Compound of Formula (IX)

Preparation Example 4-1: 2-(1-((3,4-bis (methoxymethoxy)phenyl)(6-ethylbenzo[d]thiazol-2-yl)methyl)-1H-1,2,3-triazol-4-yl)-N,N-dimethyl-ethan-1-amine (IX-1

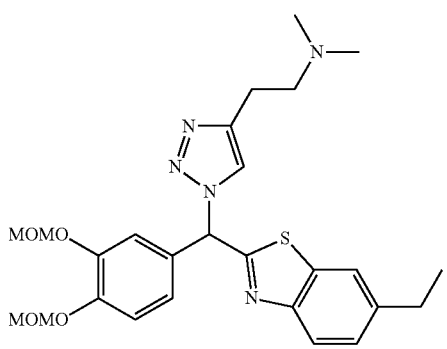

To a stirred solution of the compound (VII-2) obtained in Preparation Example 3-2 (86 mg, 0.13 mmol) in 1 mL of MeCN was added dimethylamine (98 μl, 0.78 mmol, 40 wt % solution in H₂O), and the mixture was stirred at room temperature for 15 hours. The reaction product was diluted with H₂O, and extracted with CH₂Cl₂. The organic layer was dried over MgSO₄ and concentrated in vacuo. The crude product was separated by silica gel column chromatography (CH₂Cl₂/MeOH, 10:1) to give the title compound (IX-1) (43 mg, 65%) as a yellow oil.

¹H NMR (300 MHz, CDCl₃) δ 7.91 (d, J=8.4 Hz, 1H), 7.64 (d, J=0.9 Hz, 1H), 7.60 (s, 1H), 7.31 (dd, J=1.6 Hz, 8.2 Hz, 1H), 7.24-7.21 (m, 2H), 7.13 (d, J=8.4 Hz, 1H), 6.97 (dd, J=2.1 Hz, 8.4 Hz, 1H), 5.20 (s, 2H), 5.15 (s, 2H), 3.46 (s, 3H), 3.44 (s, 3H), 2.95-2.90 (m, 2H), 2.78-2.66 (m, 4H), 2.31 (s, 3H), 1.25 (t, J=7.6 Hz, 3H);

¹³C NMR (75 MHz, CDCl₃) δ 165.8, 151.7, 148.1, 147.3, 145.7, 142.5, 135.5, 130.0, 127.0, 123.2, 122.3, 121.3, 120.1, 116.9, 116.5, 95.5, 95.1, 65.4, 58.6, 56.2, 45.0, 28.9, 23.9, 15.7;

IR (CHCl₃) ν$_{max}$ 2932, 1736, 1510, 1257, 1152, 1074, 984, 824 (cm⁻¹);

HRMS (FAB): calcd. for C₂₆H₃₄N₅O₄S [M+H]⁺ 512.2332, found 512.2327.

Preparation Example 4-2: 2-(1-((3,4-bis (methoxymethoxy)phenyl)(6-ethylbenzo[d]oxazol-2-yl)methyl)-1H-1,2,3-triazol-4-yl)-N,N-dimethyl-ethan-1-amine (IX-2

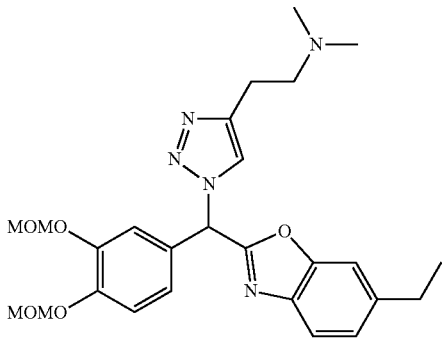

The title compound was synthesized in the same manner as in Preparation Example 4-1, except for using the compound (VII-3) obtained in Preparation Example 3-3 (64 mg, 0.10 mmol). The crude product was separated by silica gel column chromatography (CH₂Cl₂/MeOH, 10:1) to give the title compound (IX-2) (31 mg, 62%) as a yellow oil.

¹H NMR (300 MHz, CDCl₃) δ 8.35 (s, 1H), 7.68-7.60 (m, 2H), 7.32 (d, J=1.2 Hz, 1H), 7.21-7.15 (m, 2H), 7.07 (s, 1H), 6.96 (dd, J=2.2 Hz, 8.5 Hz, 1H), 5.19-5.13 (m, 4H), 3.44 (s, 3H), 3.43 (s, 3H), 3.03-2.88 (m, 2H), 2.77-2.66 (m, 4H), 2.33 (s, 3H), 2.30 (s, 3H), 1.24 (t, J=7.6 Hz, 3H);

¹³C NMR (75 MHz, CDCl₃) δ 160.4, 151.1, 150.7, 148.2, 147.4, 146.5, 145.9, 144.1, 143.1, 138.4, 130.4, 128.0, 125.1, 122.0, 121.2, 120.2, 116.8, 115.8, 109.7, 95.5, 61.7, 58.5, 56.2, 48.7, 45.0, 29.1, 15.8;

IR (CHCl₃) ν$_{max}$ 2934, 1635, 1512, 1259, 1155, 1077, 989 (cm⁻¹);

HRMS (FAB): calcd. for C₂₆H₃₄N₅O₅ [M+H]⁺ 496.2560, found 496.2560.

Example 1

4-((4-(2-(dimethylamino)ethyl)-1H-1,2,3-triazol-1-yl)(6-ethylbenzo[d]thiazol-2-yl)methyl)benzene-1,2-diol (I-1

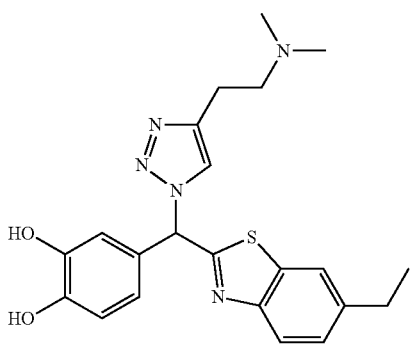 [SMILES: CCc1ccc2nc(C(c3ccc(O)c(O)c3)n3cc(CCN(C)C)nn3)sc2c1]

To a stirred solution of the compound (IX-1) obtained in Preparation Example 4-1 (32 mg, 0.063 mmol) in 0.5 mL of MeOH was added p-TsOH·H₂O (30 mg, 0.16 mmol), and the mixture was stirred at room temperature for 5 hours. The reaction product was diluted with H₂O, and extracted with EtOAc. The organic layer was dried over MgSO₄ and concentrated in vacuo. The crude product was washed with diethyl ether several times to give the title compound (I-1) (24 mg, 90%) as a brown gum.

$^1$H NMR (600 MHz, CD$_3$OD) δ 7.93 (s, 1H), 7.59 (d, J=8.2 Hz, 1H), 7.52-7.49 (m, 1H), 7.45 (s, 1H), 7.27 (dd, J=8.2 Hz, 11.9 Hz, 1H), 6.87 (d, J=1.3 Hz, 1H), 6.81-6.77 (m, 2H), 3.13 (t, J=7.3 Hz, 2H), 3.05 (t, J=7.5 Hz, 2H), 2.79-2.74 (m, 2H), 2.66 (s, 6H), 1.26 (t, J=7.5 Hz, 3H);

$^{13}$C NMR (150 MHz, CD$_3$OD) δ 163.9, 153.4, 151.4, 148.9, 148.0, 145.9, 145.6, 144.0, 140.3, 128.2, 127.2, 124.7, 122.1, 121.4, 120.5, 117.5, 117.2, 112.4, 111.7, 59.4, 45.2, 30.8, 23.7, 17.2;

IR (CHCl$_3$) ν$_{max}$ 3140 (br), 2968, 1733, 1455, 1236, 1119, 751 (cm$^{-1}$);

HRMS (FAB): calcd. for C$_{22}$H$_{26}$N$_5$O$_2$S [M+H]$^+$ 424.1807, found 424.1811.

Example 2

2-(1-((3,4-dimethoxyphenyl)(6-ethylbenzo[d]thiazol-2-yl)methyl)-1H-1,2,3-triazol-4-yl)-N,N-dimethylethan-1-amine (I-2

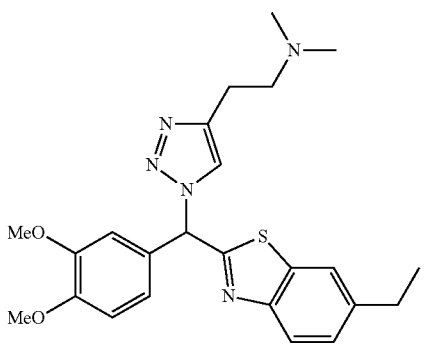 [SMILES: CCc1ccc2nc(C(c3ccc(OC)c(OC)c3)n3cc(CCN(C)C)nn3)sc2c1]

The compound (VII-1) obtained in Preparation Example 3-1 (30 mg, 0.052 mmol) was added to 0.5 mL of MeCN, and dimethylamine (65 μl, 0.52 mmol, 40 wt % solution in H₂O) was added thereto. The mixture was stirred at 40° C. for 12 hours. The reaction product was diluted with H₂O, and extracted with CH₂Cl₂. The organic layer was dried over MgSO₄ and concentrated in vacuo. The crude product was separated by silica gel column chromatography (CH₂Cl₂/MeOH, 10:1) to give the title compound (I-2) (17 mg, 72%) as a yellow gum.

$^1$H NMR (600 MHz, CDCl$_3$) δ 7.92 (d, J=8.3 Hz, 1H), 7.64 (d, J=4.6 Hz, 2H), 7.33 (dd, J=1.6 Hz, 8.5 Hz, 1H), 6.93-6.91 (m, 3H), 6.83 (d, J=8.3 Hz, 1H), 3.85 (s, 3H), 3.80 (s, 3H), 3.04 (t, J=8.0 Hz, 2H), 2.89 (brs, 2H), 2.76 (q, J=7.6 Hz, 2H), 2.45 (s, 6H), 1.27 (t, J=7.6 Hz, 3H);

$^{13}$C NMR (150 MHz, CDCl$_3$) δ 165.8, 151.2, 149.9, 149.4, 142.6, 135.6, 128.4, 127.1, 125.8, 123.3, 121.7, 120.7, 120.2, 111.2, 65.6, 58.1, 56.0, 55.9, 44.5, 28.9, 15.7;

IR (CHCl$_3$) ν$_{max}$ 2932, 1516, 1461, 1263, 1144, 1025 (cm$^{-1}$);

HRMS (FAB): calcd. for C$_{24}$H$_{30}$N$_4$O$_2$S [M+H]$^+$ 452.2120, found 452.2107.

Example 3

N-(2-(1-((3,4-dimethoxyphenyl)(6-ethylbenzo[d]thiazol-2-yl)methyl)-1H-1,2,3-triazol-4-yl) ethyl) propan-1-amine (I-3

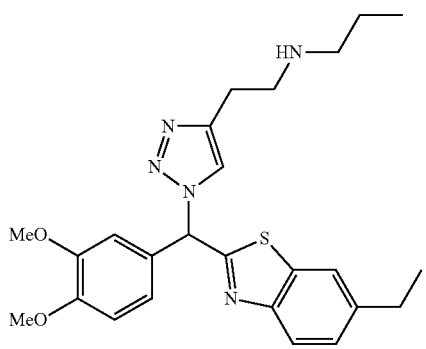 [SMILES: CCCNCCc1cn(C(c2ccc(OC)c(OC)c2)c2nc3ccc(CC)cc3s2)nn1]

The title compound was synthesized in the same manner as in Example 2, except for using the compound (VII-1) obtained in Preparation Example 3-1 (32 mg, 0.055 mmol) and propylamine (45 μl, 0.55 mmol). The crude product was separated by silica gel column chromatography (CH₂Cl₂/MeOH, 10:1) to give the title compound (I-3) (19 mg, 75%) as a yellow gum.

$^1$H NMR (300 MHz, CD$_3$OD) δ 8.07 (s, 1H), 7.85 (d, J=8.5 Hz, 1H), 7.79 (s, 1H), 7.38 (dd, J=1.6 Hz, 8.5 Hz, 1H), 7.17 (d, J=2.1 Hz, 1H), 7.07 (dd, J=2.1 Hz, 8.3 Hz, 1H), 6.99 (d, J=8.3 Hz, 1H), 3.83 (s, 3H), 3.78 (s, 3H), 3.23 (t, J=7.1 Hz, 2H), 3.07 (t, J=7.1 Hz, 2H), 2.91-2.86 (m, 2H), 2.77 (q, J=7.5 Hz, 2H), 1.70-1.62 (m, 2H), 1.27 (t, J=7.5 Hz, 3H), 0.98 (t, J=7.5 Hz, 3H);

$^{13}$C NMR (75 MHz, CD$_3$OD) δ 169.6, 152.9, 152.4, 151.6, 145.5, 144.9, 137.7, 130.5, 129.1, 125.1, 124.5, 123.4, 122.3, 114.0, 113.6, 57.3, 57.2, 51.7, 30.6, 24.8, 22.1, 17.1, 12.2;

IR (CHCl$_3$) ν$_{max}$ 3404 (br), 2962, 1594, 1516, 1459, 1261, 1144, 1024, 826 (cm$^{-1}$);

HRMS (FAB): calcd. for C$_{25}$H$_{32}$N$_5$O$_2$S [M+H]$^+$ 466.2277, found 466.2267.

Example 4

N-(2-(1-((3,4-dimethoxyphenyl)(6-ethylbenzo[d]thiazol-2-yl)methyl)-1H-1,2,3-triazol-4-yl) ethyl) cyclopentanamine (I-4

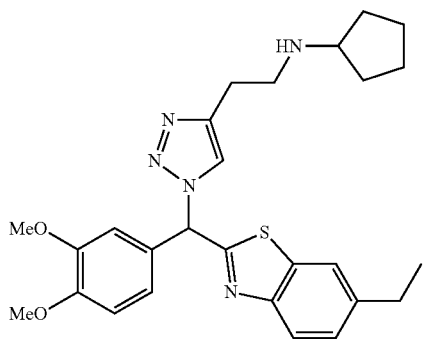 [SMILES: CCc1ccc2nc(C(c3ccc(OC)c(OC)c3)n3cc(CCNC4CCCC4)nn3)sc2c1]

The title compound was synthesized in the same manner as in Example 2, except for using the compound (VII-1) obtained in Preparation Example 3-1 (36 mg, 0.062 mmol) and cyclopentylamine (61 μl, 0.62 mmol). The crude product was separated by silica gel column chromatography (CH$_2$Cl$_2$/MeOH, 10:1) to give the title compound (I-4) (27 mg, 88%) as a yellow gum.

$^1$H NMR (300 MHz, CDCl$_3$) δ 7.91 (d, J=8.1 Hz, 1H), 7.69 (s, 1H), 7.63 (d, J=0.9 Hz, 1H), 7.31 (dd, J=1.6 Hz, 8.4 Hz, 1H), 7.22 (s, 1H), 6.94-6.89 (m, 2H), 6.82 (d, J=8.1 Hz, 1H), 3.84 (s, 3H), 3.80 (s, 3H), 3.37-3.23 (m, 5H), 2.74 (q, J=7.5 Hz, 2H), 2.05-1.93 (m, 2H), 1.79-1.67 (m, 4H), 1.57-1.51 (m, 2H), 1.25 (t, J=7.5 Hz, 3H);

$^{13}$C NMR (75 MHz, CDCl$_3$) δ 165.6, 151.0, 149.8, 149.3, 145.5, 144.1, 142.5, 135.5, 128.0, 127.1, 123.2, 122.0, 120.8, 120.1, 111.1, 65.6, 59.6, 56.0, 55.9, 46.3, 30.7, 28.9, 23.8, 15.8;

IR (CHCl$_3$) ν$_{max}$ 3410 (br), 2961, 1515, 1456, 1260, 1143, 1024, 754 (cm$^{-1}$);

HRMS (FAB): calcd. for C$_{27}$H$_{34}$N$_5$O$_2$S [M+H]$^+$ 492.2433, found 492.2437.

Example 5

2-((3,4-dimethoxyphenyl)(4-(2-(pyrrolidin-1-yl) ethyl)-1H-1,2,3-triazol-1-yl)methyl)-6-ethylbenzo[d] thiazole (I-5

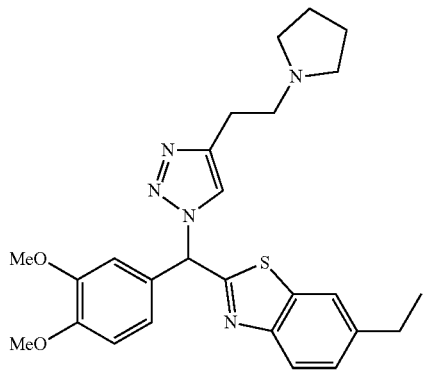 [SMILES: CCc1ccc2nc(C(c3ccc(OC)c(OC)c3)n3cc(CCN4CCCC4)nn3)sc2c1]

The title compound was synthesized in the same manner as in Example 2, except for using the compound (VII-1) obtained in Preparation Example 3-1 (32 mg, 0.055 mmol) and pyrrolidine (46 μl, 0.55 mmol). The crude product was separated by silica gel column chromatography (CH$_2$Cl$_2$/MeOH, 10:1) to give the title compound (I-5) (14 mg, 52%) as a yellow gum.

$^1$H NMR (300 MHz, CDCl$_3$) δ 7.92 (d, J=8.4 Hz, 1H), 7.66-7.64 (m, 2H), 7.32 (dd, J=1.6 Hz, 8.4 Hz, 1H), 6.93-6.88 (m, 2H), 6.83 (d, J=8.9 Hz, 1H), 3.85 (s, 3H), 3.81 (s, 3H), 3.15-3.08 (m, 4H), 2.84-2.72 (m, 6H), 1.85-1.95 (m, 4H), 1.26 (t, J=7.5 Hz, 3H);

$^{13}$C NMR (75 MHz, CDCl$_3$) δ 165.7, 151.1, 149.9, 149.4, 142.6, 135.5, 128.3, 127.1, 123.3, 121.8, 120.7, 120.1, 111.2, 111.1, 65.6, 56.0, 55.9, 55.0, 54.0, 28.9, 23.4, 15.7;

IR (CHCl$_3$) ν$_{max}$ 2962, 1603, 1514, 1456, 1259, 1143, 1024, 825, 750 (cm$^{-1}$);

HRMS (FAB): calcd. for C$_{26}$H$_{32}$N$_5$O$_2$S [M+H]$^+$ 478.2277, found 478.2277.

Example 6

4-(2-(1-((3,4-dimethoxyphenyl)(6-ethylbenzo[d] thiazol-2-yl)methyl)-1H-1,2,3-triazol-4-yl)ethyl) morpholine (I-6

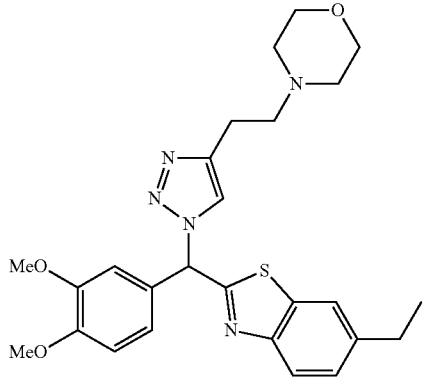 [SMILES: CCc1ccc2nc(C(c3ccc(OC)c(OC)c3)n3cc(CCN4CCOCC4)nn3)sc2c1]

The title compound was synthesized in the same manner as in Example 2, except for using the compound (VII-1) obtained in Preparation Example 3-1 (30 mg, 0.052 mmol) and morpholine (45 μl, 0.52 mmol). The crude product was separated by silica gel column chromatography (CH$_2$Cl$_2$/MeOH, 10:1) to give the title compound (I-6) (22 mg, 87%) as a yellow gum.

$^1$H NMR (300 MHz, CDCl$_3$) δ 7.92 (d, J=8.7 Hz, 1H), 7.65 (s, 1H), 7.61 (s, 1H), 7.32 (dd, J=1.3 Hz, 8.5 Hz, 1H), 7.25 (s, 2H), 6.92 (s, 1H), 6.89 (d, J=2.1 Hz, 1H), 6.82 (d, J=8.7 Hz, 1H), 3.85 (s, 3H), 3.79 (s, 3H), 3.68 (t, J=4.6 Hz, 4H), 2.92 (t, J=7.6 Hz, 2H), 2.75 (q, J=7.5 Hz, 2H), 2.68 (t, J=7.6 Hz, 2H), 2.48 (t, J=4.4 Hz, 4H), 1.26 (t, J=7.5 Hz, 3H);

$^{13}$C NMR (75 MHz, CDCl$_3$) δ 165.9, 151.1, 149.7, 149.2, 145.9, 142.5, 135.5, 128.4, 127.0, 123.2, 121.4, 120.5, 120.1, 111.0, 66.8, 65.4, 57.8, 56.0, 55.9, 53.4, 28.9, 23.2, 15.8;

IR (CHCl$_3$) ν$_{max}$ 2961, 1595, 1514, 1456, 1259, 1115, 1024, 747 (cm$^{-1}$);

HRMS (FAB): calcd. for C$_{26}$H$_{32}$N$_5$O$_3$S [M+H]$^+$ 494.2226, found 494.2239.

Example 7

2-((3,4-dimethoxyphenyl)(4-(2-(piperidin-1-yl) ethyl)-1H-1,2,3-triazol-1-yl)methyl)-6-ethylbenzo[d] thiazole (I-7

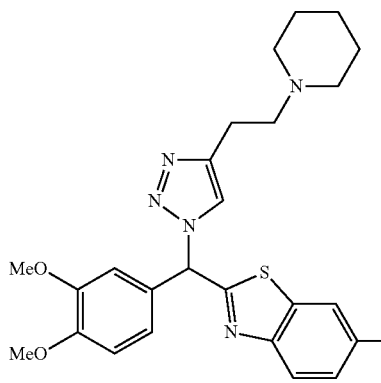

The title compound was synthesized in the same manner as in Example 2, except for using the compound (VII-1) obtained in Preparation Example 3-1 (35 mg, 0.06 mmol) and piperidine (60 µl, 0.60 mmol). The crude product was separated by silica gel column chromatography (CH$_2$Cl$_2$/MeOH, 10:1) to give the title compound (I-7) (15 mg, 50%) as a yellow solid.

mp 59.5-61.7° C.;

$^1$H NMR (300 MHz, CDCl$_3$) δ 7.92 (d, J=8.7 Hz, 1H), 7.64 (s, 1H), 7.63 (s, 1H), 7.32 (dd, J=1.6 Hz, 8.5 Hz, 1H), 6.92 (s, 2H), 6.90 (d, J=2.1 Hz, 1H), 6.82 (d, J=8.7 Hz, 1H), 3.85 (s, 3H), 3.80 (s, 3H), 3.06-2.98 (m, 2H), 2.79-2.72 (m, 4H), 2.58 (brs, 3H), 1.66 (brs, 4H), 1.46 (brs, 3H), 1.26 (t, J=7.5 Hz, 3H);

$^1$H NMR (75 MHz, CDCl$_3$) δ 165.8, 151.1, 149.7, 149.3, 142.5, 135.5, 128.4, 127.1, 123.3, 121.6, 120.6, 120.1, 111.1, 111.0, 65.5, 58.0, 55.9, 55.3, 54.3, 28.9, 25.1, 23.7, 22.8, 15.8;

IR (CHCl$_3$) $\nu_{max}$ 2933, 1595, 1515, 1455, 1259, 1144, 1025, 825, 751 (cm$^{-1}$);

HRMS (FAB): calcd. for C$_{27}$H$_{34}$N$_5$O$_2$S [M+H]$^+$ 492.2433, found 492.2425.

Preparation Example 5: Preparation of Compound of Formula (XII)

Preparation Example 5-1: (3,4-bis(benzyloxy)phenyl)(6-ethylbenzofuran-2-yl)methanone (XII-1

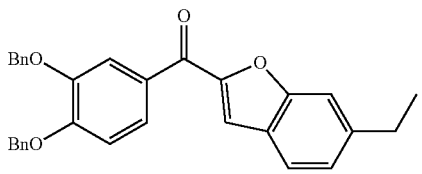 [SMILES: CCc1ccc2cc(C(=O)c3ccc(OCc4ccccc4)c(OCc4ccccc4)c3)oc2c1]

To a stirred solution of 1-(3,4-bis(benzyloxy)phenyl)-2-bromoethanone (300 mg, 0.73 mmol) in 8 mL of acetone were added 4-ethylsalicylaldehyde (110 mg, 0.73 mmol) and K$_2$CO$_3$ (101 mg, 0.73 mmol), and the mixture was refluxed for 9 hours. After cooling to room temperature, the reaction product was diluted with H$_2$O, and extracted with EtOAc. The organic layer was dried over MgSO$_4$ and concentrated in vacuo. The crude product was separated by silica gel column chromatography (hexane/EtOAc, 5:1) to give the title compound (XII-1) (293 mg, 87%) as a yellow solid.

mp 93.7-96.5° C.;

$^1$H NMR (300 MHz, CDCl$_3$) δ 8.21-7.79 (m, 13H), 7.73-7.64 (m, 3H), 7.50 (d, J=8.4 Hz, 1H), 5.77 (s, 2H), 5.74 (s, 2H), 3.28 (q, J=7.4 Hz, 2H), 1.78 (t, J=7.4 Hz, 3H);

$^{13}$C NMR (100 MHz, CDCl$_3$) δ 182.6, 156.3, 153.0, 152.0, 148.2, 148.1, 145.4, 136.8, 136.4, 130.2, 128.6, 128.0, 127.9, 127.2, 127.0, 124.7, 124.4, 124.3, 122.7, 115.9, 115.3, 113.0, 111.1, 70.9, 70.8, 29.3, 15.6;

IR (CHCl$_3$) $\nu_{max}$ 2929, 1623, 1592, 1507, 1423, 1320, 1259, 1119, 989, 856, 693 (cm$^{-1}$);

HRMS (FAB): calcd. for C$_{31}$H$_{27}$O$_4$ [M+H]$^+$ 463.1909, found 463.1918.

Preparation Example 6: Preparation of Compound of Formula (XIII

Preparation Example 6-1: (3,4-bis(benzyloxy)phenyl)(6-ethylbenzofuran-2-yl)methanol (XIII-1

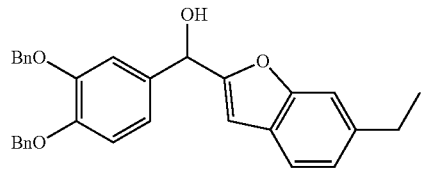 [SMILES: CCc1ccc2cc(C(O)c3ccc(OCc4ccccc4)c(OCc4ccccc4)c3)oc2c1]

A stirred solution of the compound (XII-1) obtained in Preparation Example 5-1 (280 mg, 0.61 mmol) in 3 mL of MeOH was reduced in the presence of NaBH$_4$ (23 mg, 0.61 mmol) at room temperature for 30 minutes. The reaction product was diluted with H$_2$O, and extracted with EtOAc. The organic layer was dried over MgSO$_4$ and concentrated in vacuo. The crude product was separated by silica gel column chromatography (hexane/EtOAc, 4:1) to give the title compound (XIII-1) (275 mg, 98%) as a pale yellow solid.

mp 82.5-85.3° C.;

$^1$H NMR (400 MHz, CDCl$_3$) δ 7.43-7.21 (m, 12H), 7.14 (d, J=1.2 Hz, 1H), 7.04 (dd, J=0.9 Hz, 7.9 Hz, 1H), 6.99 (s, 2H), 6.37 (s, 1H), 5.73 (s, 1H), 5.11 (s, 2H), 5.09 (s, 2H), 2.71 (q, J=7.6 Hz, 2H), 1.24 (t, J=7.6 Hz, 3H);

$^{13}$C NMR (75 MHz, CDCl$_3$) δ 155.7, 154.3, 149.4, 148.9, 141.6, 137.0, 129.3, 128.5, 127.8, 127.4, 127.2, 125.3, 123.3, 120.9, 120.7, 114.6, 114.4, 111.0, 110.3, 105.2, 71.3, 62.3, 29.0, 15.9;

IR (CHCl$_3$) $\nu_{max}$ 3445 (br), 2929, 1734, 1603, 1508, 1427, 1258, 1119, 1012, 827, 732, 694 (cm$^{-1}$);

HRMS (FAB): calcd. for C$_{31}$H$_{28}$O$_4$ [M]$^+$ 464.1988, found 464.1984.

Preparation Example 7: Preparation of Compound of Formula (XV)

Preparation Example 7-1: 2-(1-((3,4-bis(benzyloxy)phenyl)(6-ethylbenzofuran-2-yl)methyl)-1H-1,2,3-triazol-4-yl)ethyl 4-methylbenzenesulfonate (XV-1

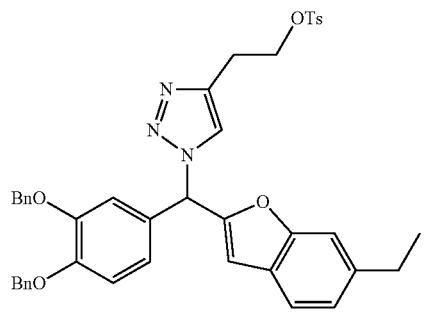 [SMILES: CCc1ccc2cc(C(c3ccc(OCc4ccccc4)c(OCc4ccccc4)c3)n3cc(CCOS(=O)(=O)c4ccc(C)cc4)nn3)oc2c1]

To a stirred solution of the compound (XIII-1) obtained in Preparation Example 6-1 (255 mg, 0.55 mmol) in 5 mL of dry MeCN was added SOCl$_2$ (48 µl, 0.66 mmol), and the mixture was stirred at room temperature for 1 hour. To the reaction mixture was added NaN$_3$ (54 mg, 0.83 mmol), and the mixture was stirred at room temperature for 4 hours. The reaction product was diluted with $H_2O$, and extracted with EtOAc. The organic layer was dried over $MgSO_4$ and concentrated in vacuo. The crude azide was used for the following reaction without additional purification.

To a solution of the obtained azide (241 mg, 0.49 mmol) in 5 mL of t-BuOH/$H_2O$ (1/1 v/v) were added 3-butynyl p-toluenesulfonate (132 mg, 0.59 mmol), sodium L-ascorbate (48 mg, 0.25 mmol) and $CuSO_4.5H_2O$ (12 mg, 0.049 mmol), and the mixture was heated to 60° C. for 2 hours. The suspension was then diluted with $H_2O$, and extracted with EtOAc. The organic layer was dried over $MgSO_4$ and concentrated in vacuo. The crude product was separated by silica gel column chromatography (hexane/EtOAc, 1.5:1) to give the title compound (XV-1) (318 mg, 81%) as a yellow oil.

$^1$H NMR (400 MHz, CDCl$_3$) δ 7.65 (d, J=8.2 Hz, 1H), 7.42-7.25 (m, 13H), 7.19 (d, J=8.1 Hz, 2H), 7.09 (d, J=7.7 Hz, 1H), 6.95 (s, 1H), 6.88 (d, J=8.3 Hz, 1H), 6.82 (d, J=1.8 Hz, 1H), 6.71 (dd, J=1.8 Hz, 8.3 Hz, 1H), 6.38 (s, 1H), 5.15 (s, 2H), 5.09 (s, 2H), 4.24 (td, J=2.6 Hz, 6.6 Hz, 2H), 3.05 (t, J=6.7 Hz, 2H), 2.74 (q, J=7.6 Hz, 2H), 2.36 (s, 3H), 1.26 (t, J=7.6 Hz, 3H);

$^{13}$C NMR (75 MHz, CDCl$_3$) δ 155.7, 155.6, 152.9, 151.7, 149.5, 149.3, 148.7, 148.5, 144.8, 143.5, 142.5, 142.1, 141.6, 136.9, 136.8, 136.7, 133.8, 132.5, 129.8, 128.5, 128.4, 127.9, 127.8, 127.7, 127.3, 127.1, 125.3, 125.0, 123.6, 123.2, 121.6, 121.0, 120.7, 114.5, 114.3, 110.4, 110.3, 107.2, 71.1, 68.7, 68.4, 60.3, 29.0, 21.6, 15.9;

IR (CHCl$_3$) $v_{max}$ 2963, 1596, 1511, 1357, 1261, 1174, 967, 735, 695 (cm$^{-1}$);

HRMS (FAB): calcd. for $C_{42}H_{39}N_3O_6S$ [M]$^+$ 713.2560, found 713.2563.

Preparation Example 8: Preparation of Compound of Formula (XVI)

Preparation Example 8-1: 2-(1-((3,4-bis(benzyloxy)phenyl)(6-ethylbenzofuran-2-yl)methyl)-1H-1,2,3-triazol-4-yl)-N,N-dimethylethan-1-amine (XVI-1

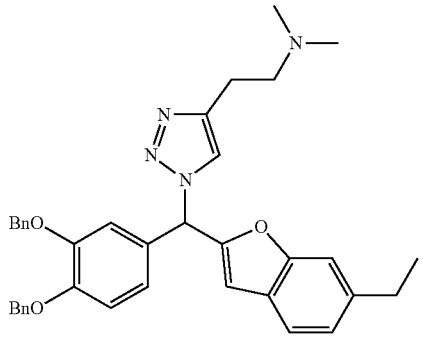 [SMILES: CCc1ccc2cc(C(c3ccc(OCc4ccccc4)c(OCc4ccccc4)c3)n3cc(CCN(C)C)nn3)oc2c1]

To a stirred solution of the compound (XV-1) obtained in Preparation Example 7-1 (210 mg, 0.29 mmol) in 1 mL of MeCN was added dimethylamine (98 μl, 0.78 mmol, 40 wt % solution in $H_2O$), and the mixture was stirred at room temperature for 15 hours. The reaction product was diluted with $H_2O$, and extracted with $CH_2Cl_2$. The organic layer was dried over $MgSO_4$ and concentrated in vacuo. The crude product was separated by silica gel column chromatography (CH$_2$Cl$_2$/MeOH, 10:1) to give the title compound (XVI-1) (120 mg, 71%) as a white solid.

mp 113.7-116.2° C.;

$^1$H NMR (400 MHz, CDCl$_3$) δ 7.42-7.26 (m, 13H), 7.08 (d, J=8.0 Hz, 1H), 6.97 (s, 1H), 6.87 (d, J=8.3 Hz, 1H), 6.81 (d, J=1.6 Hz, 1H), 6.69 (dd, J=1.7 Hz, 8.3 Hz, 1H), 6.39 (s, 1H), 5.14 (s, 2H), 5.07 (s, 2H), 2.86 (t, J=7.7 Hz, 2H), 2.74 (q, J=7.6 Hz, 2H), 2.59 (t, J=7.7 Hz, 2H), 2.27 (s, 6H), 1.26 (t, J=7.6 Hz, 3H);

$^{13}$C NMR (100 MHz, CDCl$_3$) δ 155.7, 152.2, 149.5, 148.8, 146.0, 142.0, 136.9, 136.8, 128.9, 128.5, 128.4, 127.9, 127.7, 127.3, 127.2, 125.1, 123.6, 120.9, 120.7, 120.6, 114.6, 110.4, 107.1, 71.2, 71.1, 61.9, 58.9, 45.2, 29.0, 24.2, 15.8;

IR (CHCl$_3$) $v_{max}$ 2934, 1588, 1513, 1428, 1258, 1135, 1003, 746, 696 (cm$^{-1}$);

HRMS (FAB): calcd. for $C_{37}H_{39}N_4O_3$ [M+H]$^+$ 587.3022, found 587.3007.

Example 8

4-((4-(2-(dimethylamino)ethyl)-1H-1,2,3-triazol-1-yl)(6-ethylbenzofuran-2-yl)methyl)benzene-1,2-diol (I-8

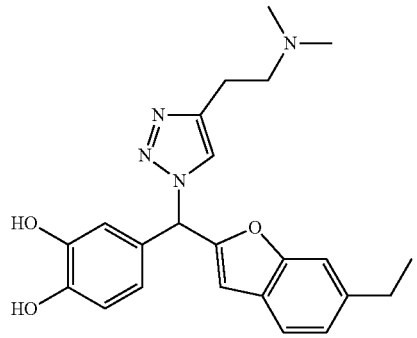 [SMILES: CCc1ccc2cc(C(c3ccc(O)c(O)c3)n3cc(CCN(C)C)nn3)oc2c1]

A stirred solution of the compound (XVI-1) obtained in Preparation Example 8-1 (54 mg, 0.092 mmol) in 0.4 mL of THF and 0.8 mL of MeOH was hydrogenated at room temperature for 1 hour under balloon pressure in the presence of 10 wt % Pd/C (23 mg). The reaction mixture was filtered over a syringe filter, and the filtrate was concentrated in vacuo to give the title compound (I-8) (34 mg, 91%) as a pale yellow oil.

$^1$H NMR (400 MHz, CDCl$_3$) δ 7.41 (s, 1H), 7.37 (d, J=8.0 Hz, 1H), 7.19 (s, 1H), 7.04 (d, J=8.0 Hz, 1H), 6.88 (s, 1H), 6.74 (d, J=8.1 Hz, 1H), 6.67 (d, J=1.7 Hz, 1H), 6.58 (dd, J=1.7 Hz, 8.1 Hz, 1H), 6.51 (s, 1H), 2.80-2.57 (m, 6H), 2.25 (s, 6H), 1.21 (t, J=7.6 Hz, 3H);

$^{13}$C NMR (100 MHz, CD$_3$OD) δ 158.0, 155.1, 148.2, 147.7, 147.2, 144.2, 129.4, 127.5, 125.4, 124.2, 122.9, 121.3, 117.3, 116.7, 111.9, 108.9, 64.4, 53.7, 30.8, 23.8, 17.3, 11.8;

IR (CHCl$_3$) $v_{max}$ 3134 (br), 2964, 1733, 1447, 1264, 1118, 1052, 816 (cm$^{-1}$);

HRMS (FAB): calcd. for $C_{23}H_{27}N_4O_3$ [M+H]$^+$ 407.2083, found 407.2072.

Example 9

4-((4-(2-(dimethylamino)ethyl)-1H-1,2,3-triazol-1-yl)(6-ethylbenzo[d]oxazol-2-yl)methyl)benzene-1,2-diol (I-9

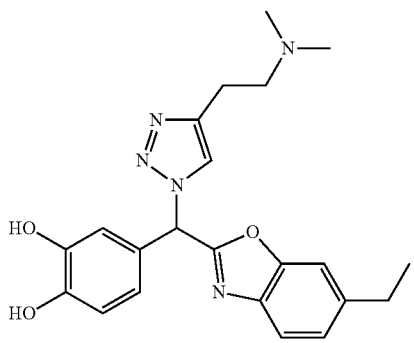 [SMILES: CCc1ccc2nc(C(c3ccc(O)c(O)c3)n3cc(CCN(C)C)nn3)oc2c1]

The title compound was synthesized in the same manner as in Example 1, except for using the compound (IX-2) obtained in Preparation Example 4-2 (20 mg, 0.040 mmol). The crude product was washed with diethyl ether several times to give the title compound (I-9) (14 mg, 85%) as a yellow gum.

$^1$H NMR (400 MHz, CDCl$_3$) δ 7.69 (s, 1H), 7.45 (s, 1H), 7.33 (d, J=8.4 Hz, 1H), 7.15 (d, J=7.0 Hz, 1H), 7.07 (s, 1H), 6.85 (d, J=1.4 Hz, 1H), 6.74 (d, J=8.2 Hz, 1H), 6.69 (dd, J=1.7 Hz, 8.1 Hz, 1H), 2.92-2.67 (m, 6H), 2.38 (s, 6H), 1.25 (t, J=7.6 Hz, 3H);

$^{13}$C NMR (75 MHz, CDCl$_3$) δ 155.7, 152.2, 149.4, 145.7, 142.1, 128.3, 125.0, 123.6, 121.0, 119.9, 111.1, 110.6, 107.1, 62.1, 55.9, 52.0, 46.7, 29.1, 23.2, 15.9, 11.2;

IR (CHCl$_3$) ν$_{max}$ 3155 (br), 2968, 1737, 1437, 1249, 1119, 819, 757 (cm$^{-1}$);

HRMS (FAB): calcd. for C$_{22}$H$_{26}$N$_5$O$_3$ [M+H]$^+$ 408.2036, found 408.2024.

Preparation Example 9: Preparation of Compound of Formula (XXI)

Preparation Example 9-1: t-butyl(2-(1-((3,4-dimethoxyphenyl)(6-ethylbenzo[d]thiazol-2-yl)methyl)-1H-imidazol-4-yl)ethyl)carbamate (XXI-1

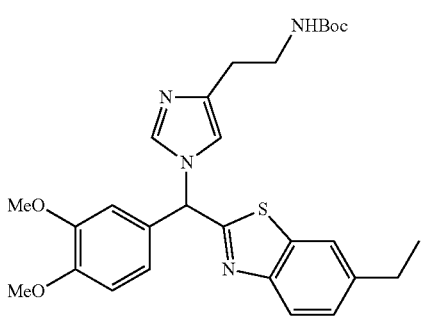 [SMILES: CCc1ccc2nc(C(c3ccc(OC)c(OC)c3)n3cnc(CCNC(=O)OC(C)(C)C)c3)sc2c1]

To a stirred solution of (6-ethylbenzo[d]thiazol-2-yl)(3,4-dimethoxyphenyl)methanol (250 mg, 0.76 mmol) in 10 mL of dry CH$_2$Cl$_2$ was added TEA (320 μl, 2.28 mmol) at 0° C. The mixture was stirred for 10 minutes, and then MsCl (71 μl, 0.912 mmol) was added thereto at 0° C. The reaction product was warmed to room temperature and stirred for 7 hours.

The solvent was evaporated, and the residue was re-dissolved in 10 mL of MeCN. t-Butyl (2-(5-iodo-1H-imidazol-4-yl)ethyl)carbamate (380 mg, 1.14 mmol) was added at room temperature, and the reaction mixture was stirred for 12 hours. The reaction product was diluted with H$_2$O, and extracted with EtOAc. The organic layer was dried over MgSO$_4$ and concentrated in vacuo. The crude product was used for the following reaction without additional purification.

To a solution of the obtained compound (206 mg, 0.32 mmol) in 3 ml of THF was added LAH (1M in THF, 0.3 mL) at 0° C., and the mixture was stirred at 0° C. for 5 minutes. The reaction product was quenched with MeOH, diluted with H$_2$O, and extracted with EtOAc. The organic layer was dried over MgSO$_4$ and concentrated in vacuo. The crude product was separated by silica gel column chromatography (EtOAc/MeOH, 50:1) to give the title compound (XXI-1) (170 mg, 50%) as a yellow oil.

$^1$H NMR (300 MHz, CDCl$_3$) δ 7.94-7.92 (d, J=8.4 Hz, 1H), 7.65 (s, 1H), 7.53 (s, 1H), 7.36-7.32 (dd, J=1.7 Hz, 8.3 Hz, 1H), 6.84-6.79 (m, 4H), 6.69 (s, 1H), 5.10 (s, 1H), 3.87 (s, 3H), 3.80 (s, 3H), 3.43-3.36 (m, 2H), 2.81-2.71 (m, 4H), 1.39 (s, 9H), 1.30-1.25 (t, J=7.5 Hz, 3H).

Preparation Example 10: Preparation of Compound of Formula (XXII

Preparation Example 10-1: 2-(1-((3,4-dimethoxyphenyl)(6-ethylbenzo[d]thiazol-2-yl)methyl)-1H-imidazol-4-yl)ethan-1-amine (XXII-1

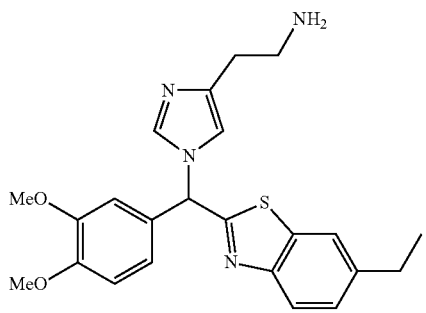 [SMILES: CCc1ccc2nc(C(c3ccc(OC)c(OC)c3)n3cnc(CCN)c3)sc2c1]

A stirred solution of the compound (XXI-1) obtained in Preparation Example 9-1 (106 mg, 0.20 mmol) in 2 ml of DCM was stirred in the presence of TFA (0.4 ml) at room temperature for 2 hours. The reaction product was quenched with saturated NaHCO$_3$ solution at 0° C., diluted with H$_2$O, and extracted with EtOAc. The organic layer was dried over MgSO$_4$ and concentrated in vacuo. The crude product was washed with ether (3×10 ml) to give the title compound (XXII-1) (77 mg, 90%) as a yellow gum.

$^1$H NMR (300 MHz, CD$_3$OD) δ 7.89 (s, 1H), 7.81 (s, 2H), 7.42-7.39 (d, J=8.4 Hz, 1H), 7.15 (s, 1H), 7.09 (s, 1H), 7.05-6.95 (m, 3H), 3.84 (s, 3H), 3.78 (s, 3H), 3.22-3.17 (m, 2H), 2.90-2.75 (m, 4H), 1.31-1.21 (t, J=7.5 Hz, 3H).

Preparation Example 10: 2-(1-((3,4-dimethoxyphenyl)(6-ethylbenzo[d]thiazol-2-yl)methyl)-1H-imidazol-4-yl)-N,N-dimethylethan-1-amine (I-10

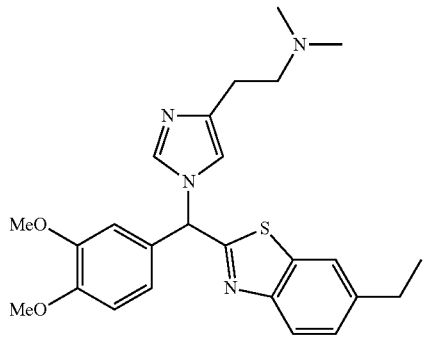 [SMILES: CCc1ccc2nc(C(c3ccc(OC)c(OC)c3)n3cnc(CCN(C)C)c3)sc2c1]

To a stirred solution of the compound (XXII-1) obtained in Preparation Example 10-1 (40 mg, 0.090 mmol) in 1 ml of MeOH were added formaldehyde (128 μl, 0.90 mmol), sodium triacethoxyborohydride (100 mg, 0.45 mmol), and AcOH (40 μl, 0.72 mmol), and the mixture was stirred at room temperature for 15 minutes. The reaction product was quenched with saturated NaHCO₃ solution at 0° C., diluted with H₂O, and extracted with EtOAc. The organic layer was dried over MgSO₄ and concentrated in vacuo. The crude product was separated by silica gel column chromatography (CH₂Cl₂/MeOH/NH₃H₂O, 30:1:1) to give the title compound (I-10) (18 mg, 40%) as a yellow oil.

¹H NMR (300 MHz, CDCl₃) δ 7.89-7.86 (d, J=8.4 Hz, 1H), 7.61 (s, 1H), 7.44 (s, 1H), 7.31-7.27 (d, J=8.4 Hz, 1H), 6.82-6.77 (m, 4H), 6.64 (s, 1H), 3.82 (s, 3H), 3.75 (s, 3H), 2.80-2.68 (m, 6H), 2.40 (s, 6H), 1.25-1.18 (t, J=7.5 Hz, 3H).

Example 11

N-(2-(1-((3,4-dimethoxyphenyl)(6-ethylbenzo[d]thiazol-2-yl)methyl)-1H-imidazol-4-yl)ethyl)-N-propylpropan-1-amine (I-11

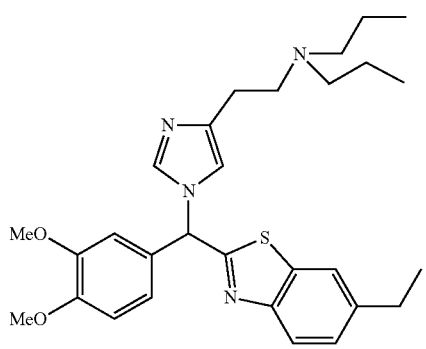 [SMILES: CCCN(CCC)CCc1cn(C(c2ccc(OC)c(OC)c2)c2nc3ccc(CC)cc3s2)cn1]

The title compound was synthesized in the same manner as in Example 10, except for using the compound (XXII-1) obtained in Preparation Example 10-1 (20 mg, 0.047 mmol) and propionaldehyde (40 μl, 0.47 mmol). The crude product was separated by silica gel column chromatography (CH₂Cl₂/MeOH/NH₃H₂O, 30:1:1) to give the title compound (I-11) (13 mg, 56%) as a yellow oil.

¹H NMR (300 MHz, CDCl₃) δ 7.89-7.86 (d, J=8.4 Hz, 1H), 7.60 (s, 1H), 7.43 (s, 1H), 7.30-7.27 (d, J=8.4 Hz, 1H), 6.81-6.72 (m, 4H), 6.64 (s, 1H), 3.82 (s, 3H), 3.74 (s, 3H), 2.76-2.68 (m, 6H), 2.44-2.38 (m, 4H), 1.48-1.36 (m, 4H), 1.25-1.17 (m, 3H), 0.81-0.76 (m, 6H).

Example 12

2-((3,4-dimethoxyphenyl)(4-(2-(piperidin-1-yl)ethyl)-1H-imidazol-1-yl)methyl)-6-ethylbenzo[d]thiazole (I-12

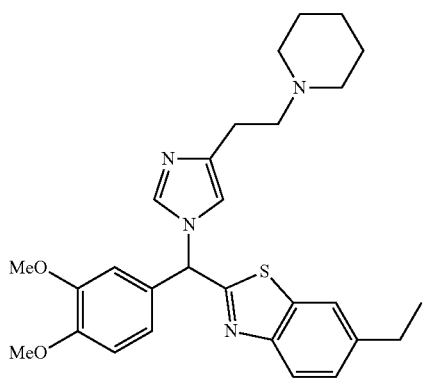 [SMILES: CCc1ccc2nc(C(c3ccc(OC)c(OC)c3)n3cnc(CCN4CCCCC4)c3)sc2c1]

The title compound was synthesized in the same manner as in Example 10, except for using the compound (XXII-1) obtained in Preparation Example 10-1 (20 mg, 0.047 mmol) and glutaraldehyde (25% in H₂O, 200 μl, 0.47 mmol). The crude product was separated by silica gel column chromatography (CH₂Cl₂/MeOH/NH₃H₂O, 30:1:1) to give the title compound (I-12) (15 mg, 65%) as a yellow oil.

¹H NMR (300 MHz, CDCl₃) δ 7.89-7.86 (d, J=8.4 Hz, 1H), 7.60 (s, 1H), 7.42 (s, 1H), 7.30-7.27 (d, J=8.4 Hz, 1H), 6.78-6.73 (m, 4H), 6.64 (s, 1H), 3.82 (s, 3H), 3.74 (s, 3H), 2.77-2.60 (m, 6H), 2.44 (m, 4H), 1.59-1.51 (m, 4H), 1.39-1.37 (m, 2H), 1.25-1.20 (t, J=7.5 Hz, 3H).

Example 13

N-(2-(1-((3,4-dimethoxyphenyl)(6-ethylbenzo[d]thiazol-2-yl)methyl)-1H-imidazol-4-yl)ethyl)cyclopentanamine (I-13

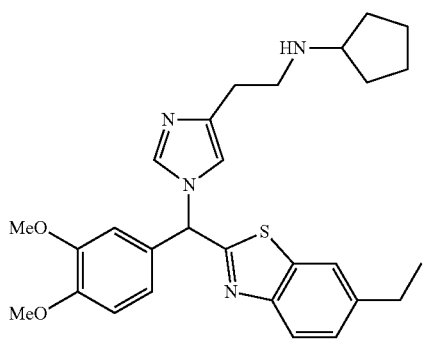 [SMILES: CCc1ccc2nc(C(c3ccc(OC)c(OC)c3)n3cnc(CCNC4CCCC4)c3)sc2c1]

To a stirred solution of the compound (XXII-1) obtained in Preparation Example 10-1 (24 mg, 0.057 mmol) in 0.5 ml of dry MeOH was added cycolpentanone (10 μl, 0.11 mmol), and the mixture was stirred at room temperature for 1 hour. Then, sodium triacetoxyborohydride (48 mg, 0.23 mmol) was added thereto, and the reactants were stirred at room temperature for 12 hours. The reaction product was diluted with H$_2$O, and extracted with EtOAc. The organic layer was dried over MgSO$_4$ and concentrated in vacuo. The crude product was separated by silica gel column chromatography (CH$_2$Cl$_2$/MeOH/NH$_3$H$_2$O, 20:4:1) to give the title compound (I-13) (17 mg, 63%) as a yellow oil.

$^1$H NMR (300 MHz, CDCl$_3$) δ 7.94-7.91 (d, J=8.4 Hz, 1H), 7.65 (s, 1H), 7.52 (s, 1H), 7.36-7.33 (d, J=8.4 Hz, 1H), 6.85 (s, 4H), 6.69 (s, 1H), 3.87 (s, 3H), 3.81 (s, 3H), 3.51-3.46 (m, 1H), 3.34-3.29 (t, J=6.2 Hz, 2H), 2.98-2.94 (t, J=6.2 Hz, 2H), 2.80-2.73 (m, 2H), 2.03-1.58 (m, 8H), 1.29-1.24 (t, J=7.5 Hz, 3H).

Example 14

2-((3,4-dimethoxyphenyl)(4-(2-(pyrrolidin-1-yl)ethyl)-1H-imidazol-1-yl)methyl)-6-ethylbenzo[d]thiazole (I-14

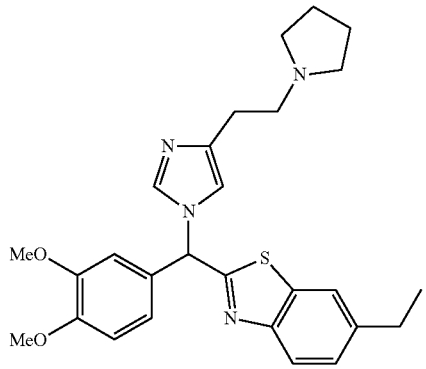 [SMILES: CCc1ccc2nc(C(c3ccc(OC)c(OC)c3)n3cnc(CCN4CCCC4)c3)sc2c1]

To a stirred solution of the compound (XXII-1) obtained in Preparation Example 10-1 (20 mg, 0.047 mmol) in 0.5 ml of MeCN were added 1,4-dibromobutane (5.6 μl, 0.047 mmol) and DIPEA (17 μl, 0.094 mmol), and the mixture was stirred at room temperature for 24 hours. The reaction product was diluted with H$_2$O, and extracted with EtOAc. The organic layer was dried over MgSO$_4$ and concentrated in vacuo. The crude product was separated by silica gel column chromatography (CH$_2$Cl$_2$/MeOH/NH$_3$H$_2$O, 30:1:1) to give the title compound (I-14) (9 mg, 41%) as a yellow oil.

$^1$H NMR (300 MHz, CDCl$_3$) δ 7.89-7.86 (d, J=8.4 Hz, 1H), 7.60 (s, 1H), 7.43 (s, 1H), 7.30-7.27 (d, J=8.4 Hz, 1H), 6.78-6.76 (m, 4H), 6.64 (s, 1H), 3.82 (s, 3H), 3.75 (s, 3H), 2.93-2.68 (m, 10H), 1.97-1.80 (m, 4H), 1.25-1.20 (t, J=7.5 Hz, 3H).

Example 15

2-((3,4-dimethoxyphenyl)(4-(piperidin-1-ylmethyl)-1H-1,2,3-triazol-1-yl)methyl)-6-ethylbenzo[d]thiazole (I-15

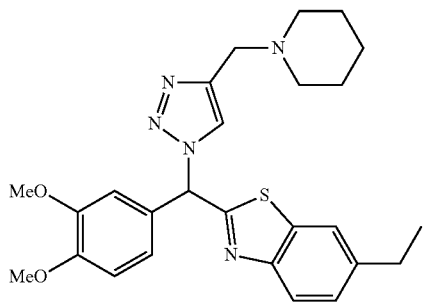 [SMILES: CCc1ccc2nc(C(c3ccc(OC)c(OC)c3)n3cc(CN4CCCCC4)nn3)sc2c1]

To a stirred solution of the compound (IV-1) obtained in Preparation Example 2-1 (331 mg, 1.0 mmol) in 8 mL of dry CH$_2$Cl$_2$ were added PPh$_3$ (633 mg, 2.41 mmol) and CBr$_4$ (800 mg, 2.41 mmol), and the mixture was stirred at room temperature for 20 minutes. To the reaction mixture was added NaN$_3$ (187 mg, 1.26 mmol), and the mixture was stirred at room temperature for 12 hours. The suspension was then filtered over a cellite pad, and the filtrate was concentrated in vacuo. The crude azide was used for the following reaction without additional purification.

To a solution of the obtained azide (36 mg, 0.11 mmol) in 12 mL of t-BuOH/H$_2$ (1/1 v/v) were added 2-propanyl p-toluenesulfonate (25 mg, 0.12 mmol), sodium L-ascorbate (10 mg, 0.05 mmol) and CuSO$_4$.5H$_2$O (13 mg, 0.049 mmol), and the mixture was heated to 60° C. for 2 hours. The suspension was then diluted with H$_2$O, and extracted with EtOAc. The organic layer was dried over MgSO$_4$ and concentrated in vacuo. The crude product was used for the following reaction without additional purification.

The obtained crude product (40 mg, 0.07 mmol) was added to 0.5 mL of MeCN, piperidine (41 μl, 0.42 mmol) was added thereto, and the mixture was stirred at 40° C. for 12 hours. The reaction product was diluted with H$_2$O, and extracted with CH$_2$Cl$_2$. The organic layer was dried over MgSO$_4$ and concentrated in vacuo. The crude product was separated by silica gel column chromatography (CH$_2$Cl$_2$/MeOH, 10:1) to give the title compound (I-15) (16 mg, 48%) as a yellow gum.

$^1$H NMR (500 MHz, CDCl$_3$) δ 7.91 (d, J=8.4 Hz, 1H), 7.76 (brs, 1H), 7.65 (s, 1H), 7.32 (dd, J=8.4 Hz, 1H), 7.27 (s, 1H), 6.93-6.91 (m, 2H), 6.82 (d, J=8.7 Hz, 1H), 3.85 (s, 3H), 3.79 (s, 3H), 3.68 (s, 2H), 2.76 (q, J=7.6 Hz, 2H), 2.45 (brs, 4H), 1.58-1.56 (m, 4H), 1.40 (brs, 2H), 1.26 (t, J=7.6 Hz, 3H).

Example 16

2-((3,4-dimethoxyphenyl)(4-(3-(piperidin-1-yl)propyl)-1H-1,2,3-triazol-1-yl)methyl)-6-ethylbenzo[d]thiazole (I-16)

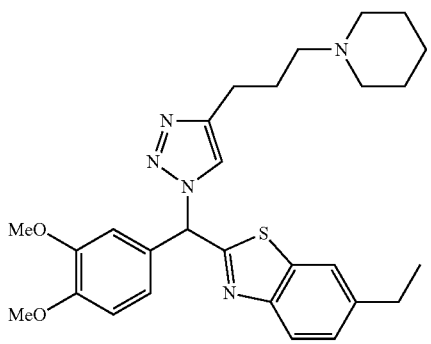 [SMILES: CCc1ccc2nc(C(c3ccc(OC)c(OC)c3)n3cc(CCCN4CCCCC4)nn3)sc2c1]

To a stirred solution of the compound (IV-1) obtained in Preparation Example 2-1 (331 mg, 1.0 mmol) in 8 mL of dry $CH_2Cl_2$ were added $PPh_3$ (633 mg, 2.41 mmol) and $CBr_4$ (800 mg, 2.41 mmol), and the mixture was stirred at room temperature for 20 minutes. To the reaction mixture was added $NaN_3$ (187 mg, 1.26 mmol), and the mixture was stirred at room temperature for 12 hours. The suspension was then filtered over a cellite pad, and the filtrate was concentrated in vacuo. The crude azide was used for the following reaction without additional purification.

To a solution of the obtained azide (38 mg, 0.11 mmol) in 12 mL of t-BuOH/$H_2O$ (1/1 v/v) were added 2-pentynyl p-toluenesulfonate (30 mg, 0.13 mmol), sodium L-ascorbate (11 mg, 0.05 mmol) and $CuSO_4 \cdot 5H_2O$ (15 mg, 0.049 mmol), and the mixture was heated to 60° C. for 2 hours. The suspension was then diluted with $H_2O$, and extracted with EtOAc. The organic layer was dried over $MgSO_4$ and concentrated in vacuo. The crude product was used for the following reaction without additional purification.

The obtained crude product (29 mg, 0.049 mmol) was added to 0.5 mL of MeCN, piperidine (29 μl, 0.294 mmol) was added thereto, and the mixture was stirred at 40° C. for 12 hours. The reaction product was diluted with $H_2O$, and extracted with $CH_2Cl_2$. The organic layer was dried over $MgSO_4$ and concentrated in vacuo. The crude product was separated by silica gel column chromatography ($CH_2Cl_2$/MeOH, 10:1) to give the title compound (I-16) (16 mg, 65%) as a yellow gum.

$^1$H NMR (500 MHz, $CDCl_3$) δ 7.93 (d, J=8.4 Hz, 1H), 7.66 (s, 1H), 7.56 (s, 1H), 7.33 (d, J=8.4 Hz, 1H), 6.93-6.90 (m, 2H), 6.83 (d, J=8.2 Hz, 1H), 3.86 (s, 3H), 3.81 (s, 3H), 2.78-2.73 (m, 4H), 2.56 (brs, 4H), 2.02-1.95 (m, 2H), 1.69 (brs, 4H), 1.47 (brs, 2H), 1.28-1.22 (m, 5H)

Experimental Example 1: In Vitro Tube Formation Assay

Matrigel (70 μl/well) was coated onto a 96-well plate and polymerized for 30 minutes at 37° C. under a 5% $CO_2$ atmosphere. HUVECs ($1.5\times10^4$ cells/well) and various concentrations of the compound were seeded onto each well of the Matrigel-coated 96-well plate. The cells were then incubated for 8 hours at 37° C. under a 5% $CO_2$ atmosphere. The formation of endothelial cell tubular structures was visualized under an inverted microscope and photographed (Olympus Optical Co. Ltd., Tokyo, Japan). The inhibition rate of tube formation was determined using the following equation.

tube formation inhibition rate (%)=[1−(average tube number$_{sample}$−average tube number$_{VEGF(-)}$)/(average tube number$_{VEGF(+)}$−average tube number$_{VEGF(-)}$)]×100    [Equation 1]

The $IC_{50}$ value was calculated using nonlinear regression analysis using TableCurve 2D v5.01 software (Systat Software Inc., Richmond, Calif., USA).

The same experiment was carried out for sunitinib as a positive control.

The results are shown in Table 1 below.

Experimental Example 2: HUVEC Cell Growth Assay

Human umbilical vascular endothelial cells (HUVECs) were obtained from the ATCC (Rockville, Md.) and cultured in EGM-2 (Lonza, Walkersville, Md.) supplemented with 10% FBS at 37° C. under a 5% $CO_2$ atmosphere.

Cell growth was assessed by MTT assay. HUVECs ($8\times10^3$ cells/well) were seeded onto a 96-well plate with EGM-2 medium supplemented with 10% FBS for 24 hours. The next day, the culture medium was removed, and the cells were then incubated with serum-free medium for 12 hours. Following serum starvation, the cells were cultured in fresh 2% FBS/EBM-2 medium containing various concentrations of the test compound for 24 hours in the presence of VEGF (50 ng/mL). After the incubation, an MTT solution was added, and the plate was incubated for additional 4 hours. The formazan product was dissolved in DMSO, and the absorbance was detected at 570 nm using a VersaMax ELISA microplate reader (Molecular Devices, Sunnyvale, Calif.).

The same experiment was carried out for sunitinib as a positive control.

The results are shown in Table 1 below.

Further, the selectivity index (SI) defined by a ratio of the $IC_{50}$ for HUVEC cell growth to the $IC_{50}$ for tube formation was calculated and the results are shown in Table 1 below.

TABLE 1

| Compound | Tube Formation $IC_{50}$ (μM) | HUVEC Cell Growth $IC_{50}$ (μM) | Selectivity Index (SI) |
|---|---|---|---|
| I-1 | 3.04 | 37.3 | 12.3 |
| I-2 | 8.27 | 93.5 | 11.3 |
| I-3 | 1.39 | 38.6 | 27.8 |
| I-4 | 1.02 | 19.4 | 19.0 |
| I-5 | 2.84 | 70.3 | 24.8 |
| I-6 | 3.93 | >100 | — |
| I-7 | 0.631 | 47.5 | 75.3 |
| I-8 | 6.10 | 22.0 | 3.61 |
| I-9 | >20 | >100 | — |
| I-10 | 4.87 | >100 | — |
| I-11 | 1.82 | 38.55 | 21.18 |
| I-12 | 3.40 | 75.59 | 22.23 |
| I-13 | 1.56 | 30.62 | 19.63 |
| I-14 | 1.53 | 95.71 | 62.56 |
| I-15 | 2.46 | >100 | 40.65 |
| I-16 | 2.28 | 30.5 | 13.38 |
| Sunitinib | 0.546 | 9.92 | 18.2 |

As shown in Table 1, the alkaloid derivative according to the present invention exhibited excellent tube formation inhibition potency without cytotoxicity to HUVECs. Particularly, the compound (I-7) of Example 7 exhibited the highest SI value of 75.3 with pronounced inhibitory activity ($IC_{50}$=0.631 μM) against tube formation. Under the same experimental conditions, the typical angiogenesis inhibitor sunitinib exhibited a much lower SI of 18.2. Sunitinib showed a similar level of inhibitory potency ($IC_{50}$=0.546 μM) against tube formation as the compound (I-7) of Example 7 but a 4.8-fold higher inhibitory effect on the cell growth of HUVECs.

Experimental Example 3: Mechanism Study

Additional scratch wound migration assay and endothelial cell tubular structure formation assay were performed with the compound (I-7) of Example 7 to understand the molecular mechanisms of the alkaloid derivative according to the present invention.

The scratch wound migration assay was performed as follows.

HUVECs were allowed to grow at 90% confluence in 12-well plates pre-coated with 0.2% gelatin and were then incubated for 24 hours. After the cells were attached, they were wounded by scratching with a 0.2 mL pipette tip. The plates were then washed with serum-free medium. Fresh medium was replaced with 2% FBS/EBM-2 medium containing various concentrations of the test compound. The cells were incubated for 24 hours, and images were recorded using an inverted phase-contrast light microscope (Olympus Optical Co. Ltd., Tokyo, Japan).

The endothelial cell tubular structure formation assay was performed in the same manner as in the Experimental Example 1.

Figure 1B:
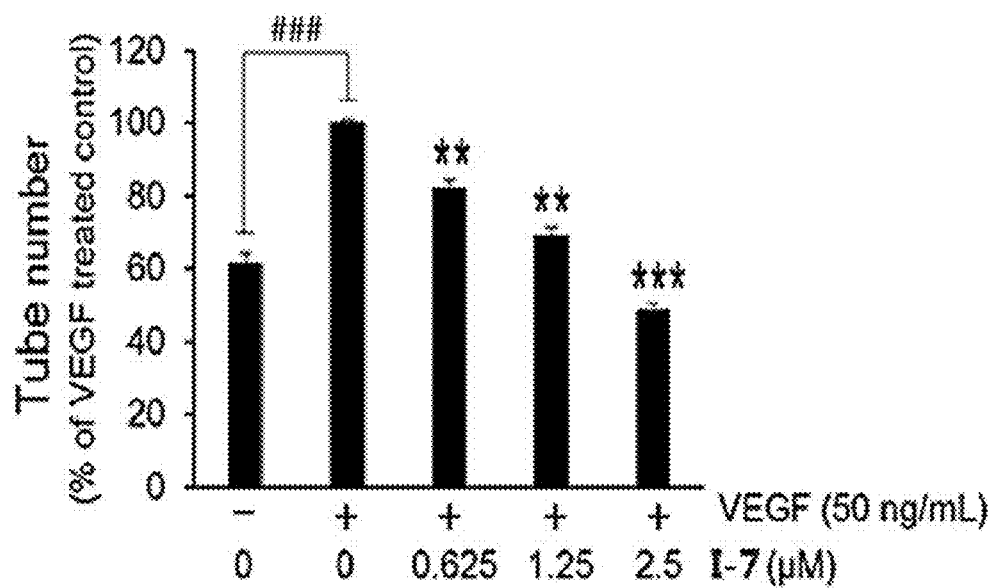
FIG. 1(B) is a graph of scratch wound migration assay of the compound (I-7) of Example 7.
Figure 1C:
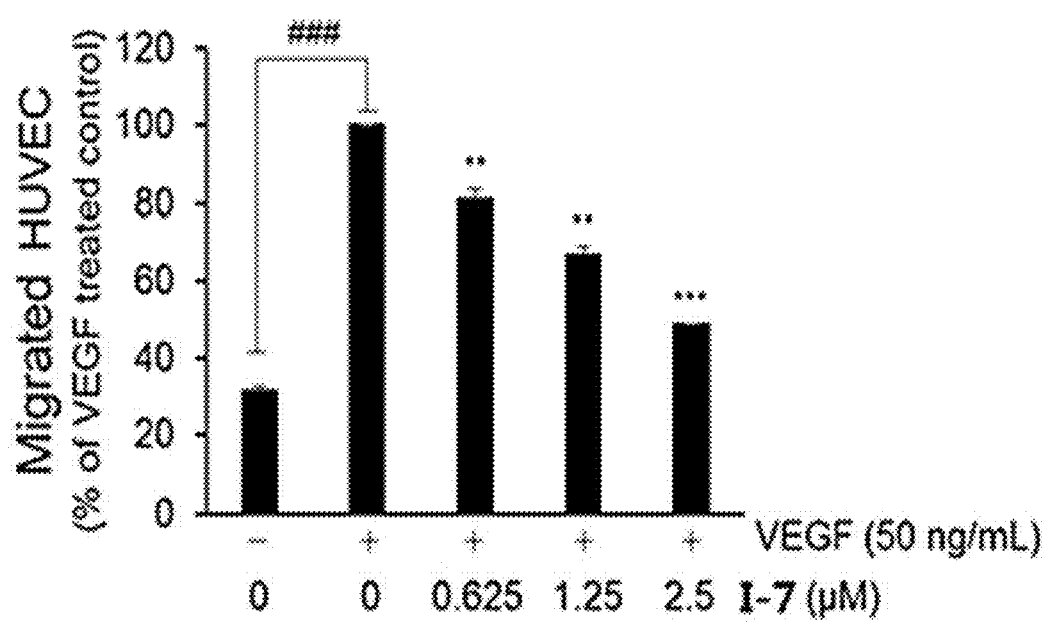
FIG. 1(C) is a graph of endothelial cell tubular structure formation assay of the compound (I-7) of Example 7.

The results are shown in FIG. 1. In the FIG. 1(A), FIG. 1(B) and FIG. 1(C). The upper panel of FIG. 1(A) and FIG. 1(B) are a photograph and graph of the endothelial cell tubular structure formation assay, respectively, and the lower panel of FIG. 1(A) and FIG. 1(C) are a photograph and graph of the scratch wound migration assay, respectively.

From the FIGS. 1(A)-1(C), it was confirmed that the enhancement of endothelial cell migration and tube formation capacity by VEGF was inhibited by the compound (I-7) of Example 7 in a concentration-dependent manner.

Further, biomarker analysis for the compound (I-7) of Example 7 was performed as follows.

The harvested cells were lysed by 2× sample loading buffer (250 mM Tris-HCl, pH 6.8; 4% SDS; 10% glycerol; 0.006% bromophenol blue; 2% β-mercaptoethanol; 50 mM sodium fluoride; and 5 mM sodium orthovanadate). The protein concentration was measured, and equal amounts of protein samples were subjected to 6-15% SDS-PAGE. The separated proteins were transferred to PVDF membranes (Millipore, Bedford, Mass.), which were then incubated with primary antibodies diluted in 2.5% BSA in TBST (1:500-1:1000) overnight at 4° C. The membranes were then washed three times with TBST and incubated with the corresponding secondary antibodies. Protein bands were detected with an enhanced chemiluminescence detection kit (Intron, Daejeon, Korea) and an LAS-4000 Imager (Fuji Film Corp., Tokyo, Japan).

Figure 2:
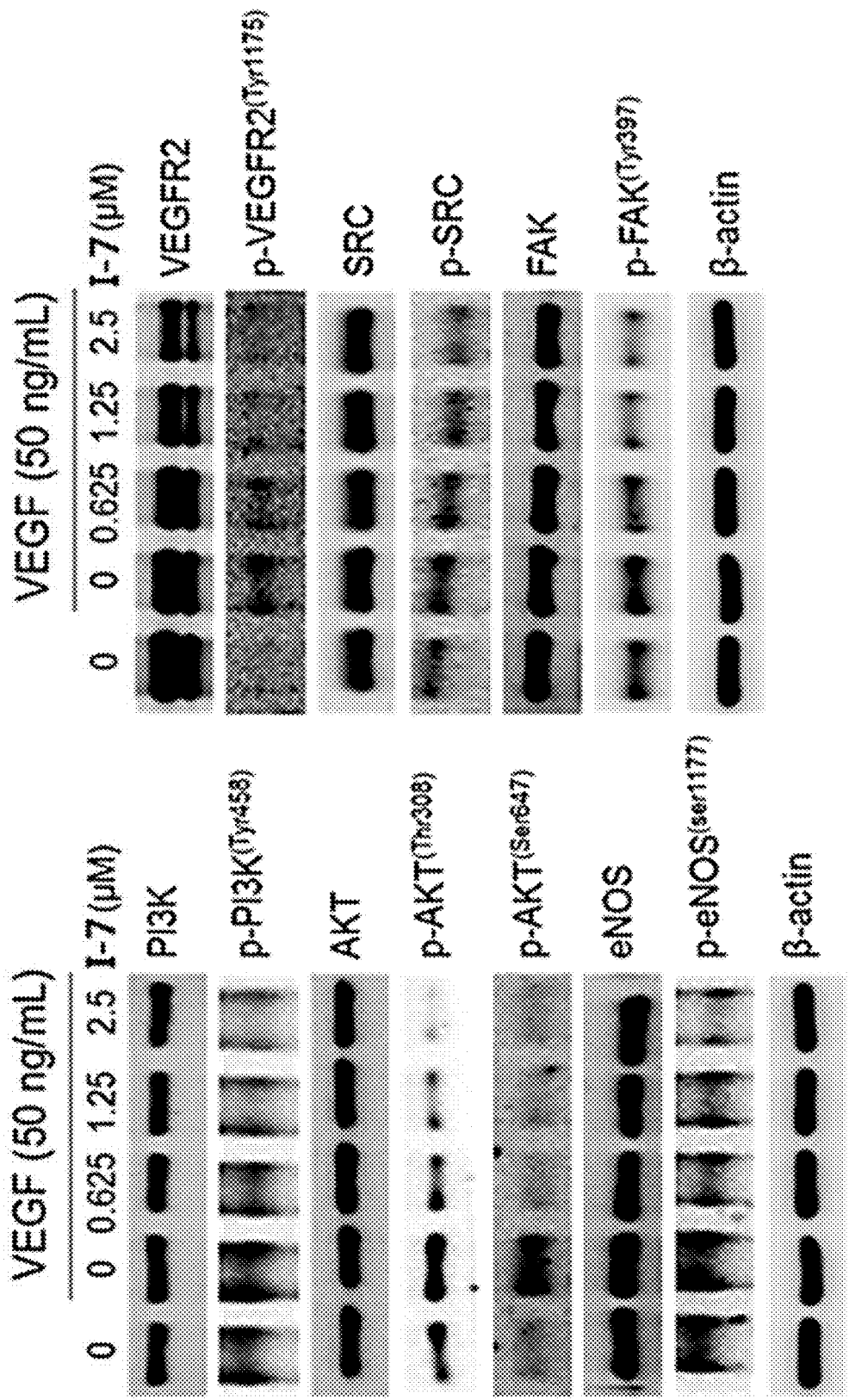
FIG. 2 is a result of biomarker analysis of the compound (I-7) of Example 7.

The results are shown in FIG. 2.

From the FIG. 2, it was confirmed that treatment of HUVECs with VEGF (50 ng/mL) for 20 minutes led to the activation of PI3K (p-PI3K), AKT (p-AKT) and eNOS (p-eNOS), whereas pretreatment with the compound (I-7) of Example 7 for 30 minutes significantly suppressed the activation processes in endothelial cells. In addition, the levels of VEGFR2 (p-VEGFR2) activated by VEGF were also suppressed by the compound (I-7) of Example 7, which subsequently inhibited the activation of SRC (p-SRC)/FAK (p-FAK) in VEGF-stimulated HUVECs. The phosphorylation of VEGFR2 (Tyr1175) affects the activation of PI3K signaling, which leads to an increase in vascular permeability. In the VEGF signaling pathway, SRC kinases are downstream of VEGFR2 and regulate vascular permeability and angiogenesis. The activation of FAK is also an important contributor markedly involved in endothelial cell migration, proliferation and adherends junction integrity. Therefore, the above results suggest that the inhibition of cell migration and neovascular tube formation by the compound (I-7) of Example 7 is partly associated with modulation of the signaling axis of VEGFR2-mediated PI3K/AKT/eNOS and the SRC/FAK signaling pathway in HUVECs.

Experimental Example 4: Preliminary ADME Study

To evaluate pharmaceutical properties of the compound (I-7) of Example 7, the aqueous solubility, permeability, plasma stability, and metabolic stability were examined as described below, and the results are shown in Table 2 below.

(1) Aqueous Solubility

The aqueous solubility was measured by the pH-metric CheqSol technique (Sirius Analytical Instruments Ltd.). Experiments was performed in 0.15 M KCl solution under a nitrogen atmosphere, at 25° C., using standardized 0.5 M HCl and 0.5 M KOH solutions.

(2) Permeability

The permeability was examined using Madin-Darby canine kidney (MDCK) cell line. The MDCK cell line was acquired from the American Type Culture Collection (Manassas, Va.). The cells were seeded in 12 well plates and allowed to grow for 7 days at 37° C. under a 5% $CO_2$ atmosphere. The MDCKI monolayers were equilibrated for 30 minutes in transport buffer (10 mM glucose, 4 mM sodium bicarbonate, HBSS with 1 mM HEPES, pH 7.4) at 37° C. under a 5% $CO_2$ atmosphere prior to the experiment. The permeability of the test compound was examined at 10 μM (with a final DMSO percentage of 1%) in the apical to basolateral (A-to-B) direction. The concentration was analyzed by LC-MS/MS. The apparent permeability ($P_{app, A-B}$) was calculated using the following equation 2.

$$P_{app, A-B} = \frac{dQ}{dt} \cdot \frac{1}{C_0} \cdot \frac{1}{A} \quad \text{[Equation 2]}$$

wherein, dQ/dt is the rate of compound appearance in the receiver compartment (Q is the quantity of compound), $C_0$ is the concentration in the donor compartment, and A is the surface area of the insert.

(3) Plasma Stability

For measuring plasma stability, the test compound (10 μM) was incubated with human plasma at 37° C. After 30 minutes, the reaction was quenched by adding acetonitrile (containing chlopropamide as internal standard). The samples were vortexed for 5 minutes and centrifuged at 14,000 rpm for 5 minutes at 4° C. Then, the supernatant was analyzed using a LC-MS/MS (Kinetex $C_{18}$ column, Phenomenex, USA).

(4) Metabolic Stability

The test compound (1 μM) was incubated with human liver microsomes (HLM, 0.5 mg protein/ml) for 5 minutes at 37° C. in 100 mM potassium phosphate buffer (pH 7.4). The reaction was initiated by adding NADPH solution and incubated for 30 minutes. To terminate the reaction, acetonitrile (containing chlopropamide as internal standard) was added and centrifuged at 14,000 rpm for 5 minutes at 4° C. Then, the supernatant was analyzed using a LC-MS/MS (Kinetex $C_{18}$ column, Phenomenex, USA).

TABLE 2

| $pK_a$ | Aqueous Solubility (mM) | MDCK $P_{app,A-B}$ ($10^{-6}$ cm/s) | Plasma Stability (%) | Metabolic Stability (%) |
|---|---|---|---|---|
| 9.24 | 0.024 | 11 | 95 | 31 |

From the Table 2, it was confirmed that the compound (I-7) of Example 7 has high plasma stability and thus it is advantageous for the achievement of in vivo activity. Specifically, the compound (I-7) of Example 7 showed plasma stability of 95% remaining intact after 30 minute incubation with human plasma. Also, the compound (I-7) of Example 7 exhibited good microsomal stability in the metabolic stability study using human liver microsomes, and exhibited high MDCK cell permeability.

Experimental Example 5: Animal Model Angiogenesis Inhibition Assay (Efficacy Assay on Diabetic Retinopathy To evaluate in vivo efficacy of the compound (I-7) of Example 7 on diabetic retinopathy, the experiment was performed as described below.

Transgenic zebrafish (flk:EGFP) embryos were provided by the Korea Zebrafish Oraganogenesis Muatant Bank (ZOMB, Daegu, Korea). The zebrafish embryos (3 dpf) were placed in a 12-well plate with 130 mM glucose embryonic $H_2O$ and various concentrations of the test compound. At 6 dpf, zebrafish larvae were fixed by 4% paraformaldehyde and stored overnight at 4° C. Next, the larvae were washed with distilled $H_2O$, incubated with 10× trypsin (2.5%) for 90 minutes at 37° C. under a 5% $CO_2$ atmosphere, and washed with distilled $H_2O$. Then, the isolated lenses were isolated from the zebrafish larvae. Optic disc (OD) branches were visualized and photographed using a fluorescence microscope (Axiovert 200M, Carl Zeiss, Del.). The diameters of the larvae vessels were measured by ImageJ software.

Figure 3A:
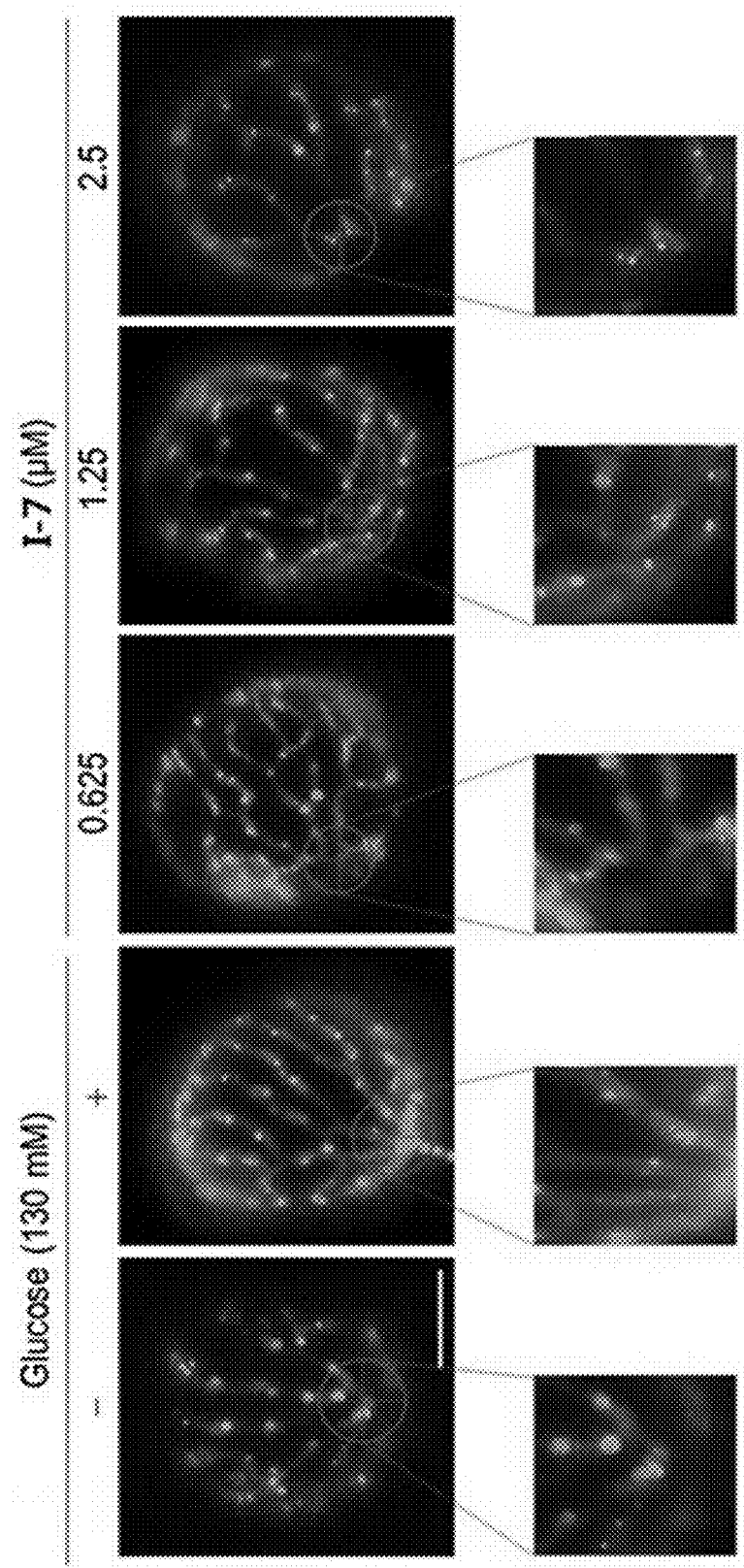
FIG. 3(A) is a photograph of animal model angiogenesis inhibition assay of the compound (I-7) of Example 7.
Figure 3B:
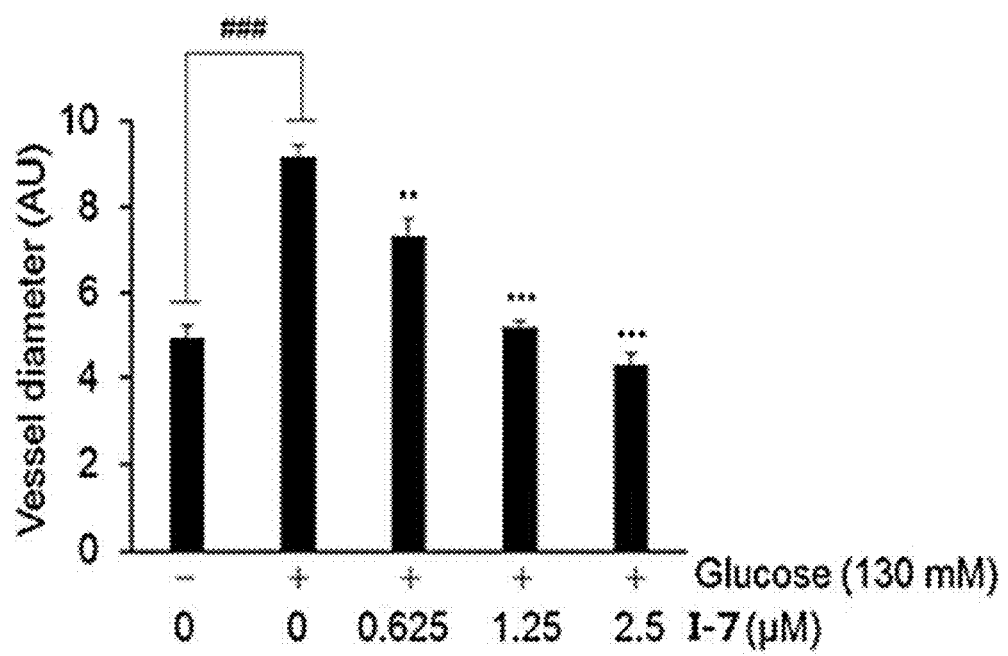
FIG. 3(B) is a graph of animal model angiogenesis inhibition assay of the compound (I-7) of Example 7.

The results are shown in the FIGS. 3(A) and 3(B).

As can be seen in the FIGS. 3(A) and 3(B), the zebrafish larvae treated with high levels of glucose (HG) exhibited significantly increased hyaloid vessel diameters in isolated eye lenses. However, treatment with the compound (I-7) of Example 7 suppressed the increase in hyaloid vessel diameters induced by HG in a concentration-dependent manner. In particular, treatment with 2.5 μM of the compound (I-7) of Example 7 markedly reduced the hyaloid vessel diameters in the optic disc area. These results suggest that the reduction in HG-induced hyaloid vessel diameters by the compound (I-7) of Example 7 is associated with anti-angiogenic activity in the in vivo animal model.

The invention claimed is:

1. An alkaloid derivative of the following formula (I) or pharmaceutically acceptable salt thereof:

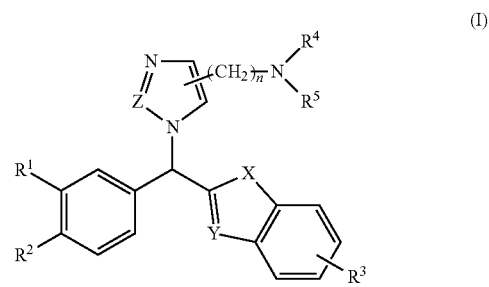

wherein,
X is oxygen or sulfur atom,
Y is nitrogen or carbon atom,
Z is nitrogen or carbon atom,
$R^1$ and $R^2$ are each independently hydrogen, hydroxyl, or $C_1$-$C_6$ alkoxy,
$R^3$ is $C_1$-$C_6$ alkyl,
$R^4$ and $R^5$ are each independently hydrogen, $C_1$-$C_6$ alkyl, or $C_3$-$C_{10}$ cycloalkyl, or
$R^4$ and $R^5$ form a 5- to 7-membered heterocycle in combination with nitrogen adjacent thereto, and
n is an integer of 0 to 6.

2. The alkaloid derivative of claim 1 or pharmaceutically acceptable salt thereof,
wherein,
X is oxygen atom,
Y is carbon atom, and
Z is nitrogen or carbon atom.

3. The alkaloid derivative of claim 1 or pharmaceutically acceptable salt thereof,
wherein,
X is sulfur atom,
Y is nitrogen atom, and
Z is nitrogen or carbon atom.

4. The alkaloid derivative of claim 1 or pharmaceutically acceptable salt thereof,
wherein,
X is sulfur atom,
Y is nitrogen atom,
Z is nitrogen or carbon atom,
$R^1$ and $R^2$ are each independently hydroxyl or $C_1$-$C_6$ alkoxy,
$R^3$ is $C_1$-$C_6$ alkyl,
$R^4$ and $R^5$ are each independently hydrogen, $C_1$-$C_6$ alkyl, or $C_3$-$C_{10}$ cycloalkyl, or
$R^4$ and $R^5$ form a 5- to 7-membered heterocycle in combination with nitrogen adjacent thereto, and
n is an integer of 0 to 6.

5. The alkaloid derivative of claim 1 or pharmaceutically acceptable salt thereof,
wherein,
X is sulfur atom,
Y is nitrogen atom,
Z is nitrogen atom,
$R^1$ and $R^2$ are each independently hydroxyl or C alkoxy,
$R^3$ is $C_1$-$C_6$ alkyl,
$R^4$ and $R^5$ are each independently hydrogen, $C_1$-$C_6$ alkyl, or $C_3$-$C_{10}$ cycloalkyl, or R⁴ and R⁵ form a 5- to 7-membered heterocycle in combination with nitrogen adjacent thereto, and n is an integer of 0 to 6.

6. The alkaloid derivative of claim 1 selected from the group consisting of the following compounds:

4-((4-(2-(dimethylamino)ethyl)-1H-1,2,3-triazol-1-yl)(6-ethylbenzo[d]thiazol-2-yl)methyl)benzene-1,2-diol;

2-(1-((3,4-dimethoxyphenyl)(6-ethylbenzo[d]thiazol-2-yl)methyl)-1H-1,2,3-triazol-4-yl)-N,N-dimethylethan-1-amine;

N-(2-(1-((3,4-dimethoxyphenyl)(6-ethylbenzo[d]thiazol-2-yl)methyl)-1H-1,2,3-triazol-4-yl)ethyl)propan-1-amine;

N-(2-(1-((3,4-dimethoxyphenyl)(6-ethylbenzo[d]thiazol-2-yl)methyl)-1H-1,2,3-triazol-4-yl)ethyl)cyclopentanamine;

2-((3,4-dimethoxyphenyl)(4-(2-(pyrrolidin-1-yl)ethyl)-1H-1,2,3-triazol-1-yl)methyl)-6-ethylbenzo[d]thiazole;

4-(2-(1-((3,4-dimethoxyphenyl)(6-ethylbenzo[d]thiazol-2-yl)methyl)-1H-1,2,3-triazol-4-yl)ethyl)morpholine;

2-((3,4-dimethoxyphenyl)(4-(2-(piperidin-1-yl)ethyl)-1H-1,2,3-triazol-1-yl)methyl)-6-ethylbenzo[d]thiazole;

4-((4-(2-(dimethylamino)ethyl)-1H-1,2,3-triazol-1-yl)(6-ethylbenzofuran-2-yl)methyl)benzene-1,2-diol;

4-((4-(2-(dimethylamino)ethyl)-1H-1,2,3-triazol-1-yl)(6-ethylbenzo[d]oxazol-2-yl)methyl)benzene-1,2-diol;

2-(1-((3,4-dimethoxyphenyl)(6-ethylbenzo[d]thiazol-2-yl)methyl)-1H-imidazol-4-yl)-N,N-dimethylethan-1-amine;

N-(2-(1-((3,4-dimethoxyphenyl)(6-ethylbenzo[d]thiazol-2-yl)methyl)-1H-imidazol-4-yl)ethyl)-N-propylpropan-1-amine;

2-((3,4-dimethoxyphenyl)(4-(2-(piperidin-1-yl)ethyl)-1H-imidazol-1-yl)methyl)-6-ethylbenzo[d]thiazole;

N-(2-(1-((3,4-dimethoxyphenyl)(6-ethylbenzo[d]thiazol-2-yl)methyl)-1H-imidazol-4-yl)ethyl)cyclopentanamine;

2-((3,4-dimethoxyphenyl)(4-(2-(pyrrolidin-1-yl)ethyl)-1H-imidazol-1-yl)methyl)-6-ethylbenzo[d]thiazole;

2-((3,4-dimethoxyphenyl)(4-(piperidin-1-ylmethyl)-1H-1,2,3-triazol-1-yl)methyl)-6-ethylbenzo[d]thiazole; and 2-((3,4-dimethoxyphenyl)(4-(3-(piperidin-1-yl)propyl)-1H-1,2,3-triazol-1-yl)methyl)-6-ethylbenzo[d]thiazole, or pharmaceutically acceptable salt thereof.

7. A pharmaceutical composition comprising the compound of claim 1 or pharmaceutically acceptable salt thereof together with a pharmaceutically acceptable carrier.

8. A method for inhibiting vascular tube formation in a subject in need thereof, comprising administering the pharmaceutical composition of claim 7 to the subject.

9. The method of claim 8, wherein the subject suffers from diabetic retinopathy, cancer, duodenal ulcer, arthritis, or obesity.

10. The method of claim 9, wherein the subject suffers from diabetic retinopathy.

* * * * *